(12) United States Patent
Bornheimer

(10) Patent No.: US 12,175,539 B2
(45) Date of Patent: Dec. 24, 2024

(54) SYSTEM AND METHODS FOR PROCESSING PLANS HAVING DATA AND CONDITIONS APPLICABLE TO A POPULATION

(71) Applicant: Zach Bornheimer, Margate, FL (US)

(72) Inventor: Zach Bornheimer, Margate, FL (US)

(*) Notice: Subject to any disclaimer, the term of this patent is extended or adjusted under 35 U.S.C. 154(b) by 236 days.

(21) Appl. No.: 17/739,663

(22) Filed: May 9, 2022

(65) Prior Publication Data

US 2022/0261923 A1    Aug. 18, 2022

Related U.S. Application Data

(63) Continuation-in-part of application No. 16/701,960, filed on Dec. 3, 2019, now abandoned.

(51) Int. Cl.
*G06Q 40/08* (2012.01)
*G16H 10/60* (2018.01)

(52) U.S. Cl.
CPC .......... *G06Q 40/08* (2013.01); *G16H 10/60* (2018.01)

(58) Field of Classification Search
CPC ........ G06Q 40/08; G16H 10/60; G16H 40/20; G16H 50/20
USPC .......................................................... 705/4
See application file for complete search history.

(56) References Cited

U.S. PATENT DOCUMENTS

| | | | |
|---|---|---|---|
| 7,860,732 B2 | 12/2010 | Elizabeth et al. | |
| 7,895,054 B2 | 2/2011 | Slen et al. | |
| 7,974,920 B2 | 7/2011 | Mehus et al. | |
| 8,126,737 B2 | 2/2012 | Slen et al. | |
| 8,265,953 B2 | 9/2012 | Elizabeth et al. | |
| 8,265,956 B2 | 9/2012 | Slen et al. | |
| 8,799,030 B1* | 8/2014 | Chen et al. | ........... G06F 19/322 |
| 2002/0111835 A1* | 8/2002 | Hele et al. | .............. G06F 17/60 705/4 |
| 2002/0116231 A1* | 8/2002 | Hele et al. | .............. G06F 17/60 705/4 |
| 2002/0120474 A1* | 8/2002 | Hele et al. | .............. G06F 17/60 705/4 |
| 2005/0261939 A1* | 11/2005 | Augspurger et al. | ... G06F 17/60 705/2 |

(Continued)

OTHER PUBLICATIONS

S. Long et al., Redesigning an Information System that Reduces Health Care Accessibility Effort and Increases User Acceptance and Satisfaction: A Comparative Effectiveness Study. Oct. 3, 2018, The Journal for Electronic Health Data and Methods, pp. 1-8. (Year: 2018).*

(Continued)

*Primary Examiner* — Scott C Anderson
*Assistant Examiner* — George N. Proios
(74) *Attorney, Agent, or Firm* — Millen, White, Zelano & Branigan P.C.; William F. Nixon

(57) ABSTRACT

A platform and associated methods manage and recommend a number of plans to a user. Processes to manage the plans access supplied user data to create a person object or representation. Parsed user data can be used. Plans are excluded using various criteria. Parameters are processed as defined in a configuration system along with checks to determine if a particular plan fits, does not fit, or is inconclusive. The determination considers, for example, conditions and medications for the user when excluding plans. Results of potential plans are provided to the user.

12 Claims, 18 Drawing Sheets

(56) References Cited

U.S. PATENT DOCUMENTS

| | | | |
|---|---|---|---|
| 2006/0293928 A1* | 12/2006 | Schumacher et al. | G06Q 40/00 705/4 |
| 2007/0233515 A1* | 10/2007 | Mehus et al. | G06F 17/60 705/4 |
| 2015/0254754 A1* | 9/2015 | Lang et al. | G06Q 30/06 |
| 2017/0039344 A1* | 2/2017 | Bitran et al. | G06F 19/3475 |
| 2019/0392931 A1* | 12/2019 | Abousy et al. | G16H 10/60 |
| 2020/0090281 A1* | 3/2020 | Tamarkin | G06Q 40/08 |

OTHER PUBLICATIONS

C. D. Anderson, et al., Rx-decision: A decision support tool for the optimal prescription drug plan for patients, Apr. 27, 2012, 2012 IEEE Systems and Information Engineering Design Symposium, Charlottesville, VA, pp. 24-29. (Year: 2012).*

A. Vij et al., Approaches Towards A Recommendation Engine For Life Insurance Products, Dec. 3, 2021, 2021 IEEE International Conference on Mobile Networks and Wireless Communications (ICMNWC), Tumkur, Karnataka, India, pp. 1-5. (Year: 2021).*

* cited by examiner

SYSTEM AND METHODS FOR PROCESSING PLANS HAVING DATA AND CONDITIONS APPLICABLE TO A POPULATION

FIELD OF THE INVENTION

The present invention relates to a system having a front end accessor and a core database along with associated methods for managing a plurality of plans having data and conditions applicable to a population.

DESCRIPTION OF THE RELATED ART

Most consumers purchase various plans, such as insurance, based on price and little other information. Consumers also have to consider a large variety of plans with numerous options and criteria. Agents are pressured to sell the plans with the most return while some companies promote cheap plans with marketing gimmicks that have no relation to the level of service or care provided. This process may not serve the consumer well or provide adequate coverage. Further, providing such plans can take time by filling out paperwork, visiting insurance agents, and the like.

SUMMARY OF THE INVENTION

A method for determining at least one plan for a user from a plurality of plans is disclosed. The method includes generating a digital personal representation of user data. The user data includes parameters that apply to an object for the personal representation. The method also includes checking to determine if a plan meets any exclusion criterion according to the parameters of the personal representation. The method also includes processing each parameter defined along with additional checks to determine whether the parameter fits according to the plan. The method also includes determining if the plan is excluded based upon the processing. The method also includes returning the plan as recommended or excluded based upon the determination.

A computing platform for determining at least one plan for a user from a plurality of plans is disclosed. The computing platform is configured to generate a digital personal representation of user data. The user data includes parameters that apply to an object for the personal representation. The computing platform also is configured to check to determine if a plan meets any exclusion criterion according to the parameters of the personal representation. The computing platform also is configured to process each parameter defined along with additional checks to determine whether the parameter fits according to the plan. The computing platform also is configured to determine if the plan is excluded based upon the processing. The computing platform also is configured to return the plan as recommended or excluded based upon the determination.

A method for processing a plurality of plans for a user is disclosed. The method includes creating a person object. The method also includes processing user data for the person object. The method also includes creating a person representation using the user data and generated missing data based on the user data. The method also includes assembling plan data structures for the plurality of plans. The method also includes determining whether the person representation meet any exclusionary criterion according to the plan data structures. The method also includes, for non-exclusionary plans, determining whether the person representation meets a criterion for each non-exclusionary plan. The method also includes returning a sorted list of determined plans.

A computing platform for processing a plurality of plans for a user is disclosed. The computing platform is configured to create a person object. The computing platform also is configured to process user data for the person object. The computing platform also is configured to create a person representation using the user data and generated missing data based on the user data. The computing platform also is configured to assemble plan data structures for the plurality of plans. The computing platform also is configured to determine whether the person representation meet any exclusionary criterion according to the plan data structures. The computing platform also is configured to, for non-exclusionary plans, determine whether the person representation meets a criterion for each non-exclusionary plan. The computing platform also is configured to return a sorted list of determined plans.

A method for sorting a plurality of plans is disclosed. The method includes processing a plurality of medications to keep only applicable medications to the personal representation. The method also includes processing a plurality of conditions to keep only applicable conditions to the personal representation. The method also includes checking that each plan of the plurality of plans has a rank that is equal or worse than the worst rank of the medications. The method also includes checking that the each plan of the plurality of plans has a rank that is equal or worse than the worst rank of the conditions. The method also includes adding the plan to a list of recommended plans based on the checking steps.

A computing platform sorting a plurality of plans is disclosed. The computing platform is configured to process a plurality of medications to keep only applicable medications. The computing platform also is configured to check that each plan of the plurality of plans has a rank that is equal or worse than the worst rank of the medications. The computing platform also is configured to process all conditions to keep only applicable conditions. The computing platform also is configured to check that the each plan of the plurality of plans has a rank that is equal or worse than the worst rank of the conditions. The computing platform also is configured to add the plan to a list of recommended plans based on the checking steps.

BRIEF DESCRIPTION OF THE DRAWINGS

Various other features and attendant advantages of the present invention will be more fully appreciated as the same becomes better understood when considered in conjunction with the accompanying drawings.

DETAILED DESCRIPTION OF THE PREFERRED EMBODIMENTS

Figure 1:
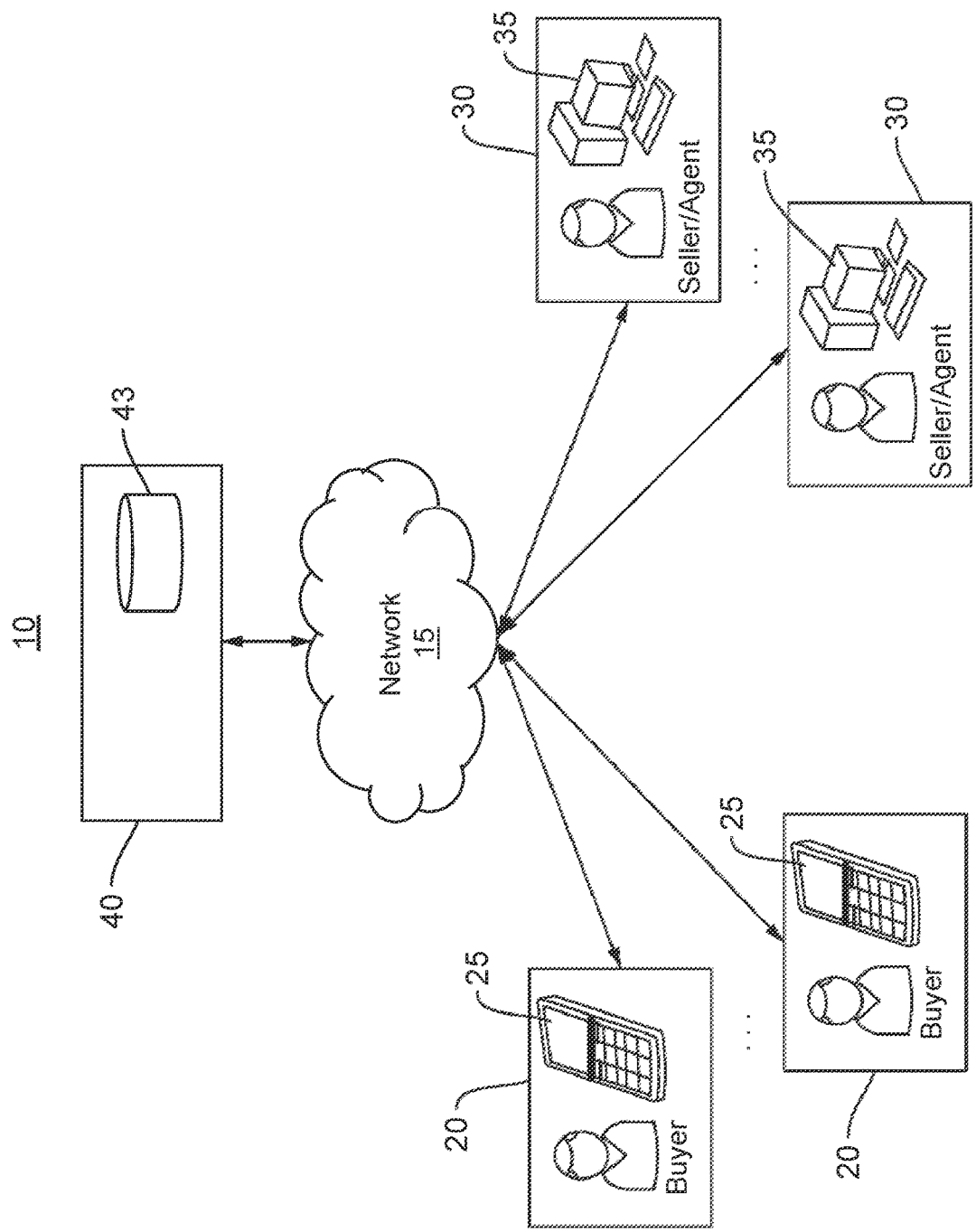
FIG. 1 illustrates a system having a plan management platform according to the disclosed embodiments.

Reference will now be made in detail to specific embodiments of the present invention. Examples of these embodiments are illustrated in the accompanying drawings. While the embodiments will be described in conjunction with the drawings, it will be understood that the following description is not intended to limit the present invention to any one embodiment. On the contrary, the following description is intended to cover alternatives, modifications, and equivalents as may be included within the spirit and scope of the appended claims. Numerous specific details are set forth in order to provide a thorough understanding of the present invention.

The disclosed embodiments implement processes using a front end component and back end component to analyze and determine appropriate plans, such as health insurance benefit plans, for a potential customer. The disclosed processes remove plans that do meet criteria set forth by the carriers of the plans using information from the potential customer as well as information from the plans themselves. The disclosed embodiments improve this process by quickly removing ineligible or inadequate plans based on factors and conditions. Using the health plan example, factors may include medicines being taken by the customer. Conditions relate to a state or "condition" of the customer. Using a banking example, factors may include income, investments, and savings while conditions pertain to debt and property owned by the customer.

The front end and back end components use functions within the program itself to dynamically identify conditions using the medicine being used by the customer as well as aliases and additional processing called only if needed to remove plans from consideration. The back end includes a database generated specifically for the processes that is encrypted and stored until needed. These features reduce the processing normally required to provide appropriate plans to an agent.

Removal of plans provides a practical application of the disclosed embodiments. An agent is not promoting or offering plans for which the customer does not qualify. Time is not wasted filling out applications and providing sensitive information only to be turned down. Moreover, confusion between different carriers, products, and plan is reduced by invoking the disclosed processes before sorting and identification of plans begins. For example, different names for medicines and conditions are resolved using the disclosed processes so that each plan is analyzed according to the same criteria. Further, additional conditions are automatically identified so that a complete medical history may be compiled before selection processing.

The disclosed embodiments further safeguard the back end component through piracy remediation measures as well as limiting access to the data and programs executing on the back end. The disclosed processes prevent unauthorized access to the proprietary features of the components as well as access to the plans and associated information. Users may not give out user name and passwords to colleagues to gain access to the databases and information available to the disclosed embodiments.

FIG. 1 depicts a system 10 having a plan management platform 40 through which potential buyers 20 and potential sellers or agents 30 may interact to provide one or more plans for purchase. Preferably, the plans relate to insurance in that different plans will apply to different consumers. The plans are not "one size fits all." The disclosed embodiments select the best plan or plans for the consumers according to processes implemented within system 10 and by platform 40. Platform 40 may access one or more networks 15. Various users of system 10, such as potential buyers 20 and sellers/agents 30 may register with platform 40. Access to platform 40 may occur by visiting a specific website via a web browser, opening and executing an application, such as a mobile or desktop application, and the like using devices 25 and 35. Devices 25 and 35 may include any computer-based system, such as a desktop computer, laptop computer, mobile computer or tablet, phone, smart device, game device or console, personal digital assistant, and the like.

Platform 40 may include storage device 43. Data storage device 43 may be a server, database, memory location, portable memory, and the like. Data storage device 43 may store user data and other information used in executing the processes disclosed below. Data storage device 43 also may store instructions, or code, that is executed on platform 40 to manage a plurality of insurance plans. In some embodiments, the insurance plans are life care insurance plans. For illustrative purposes, the disclosed embodiments will refer to life care insurance plans below.

Figure 2A:
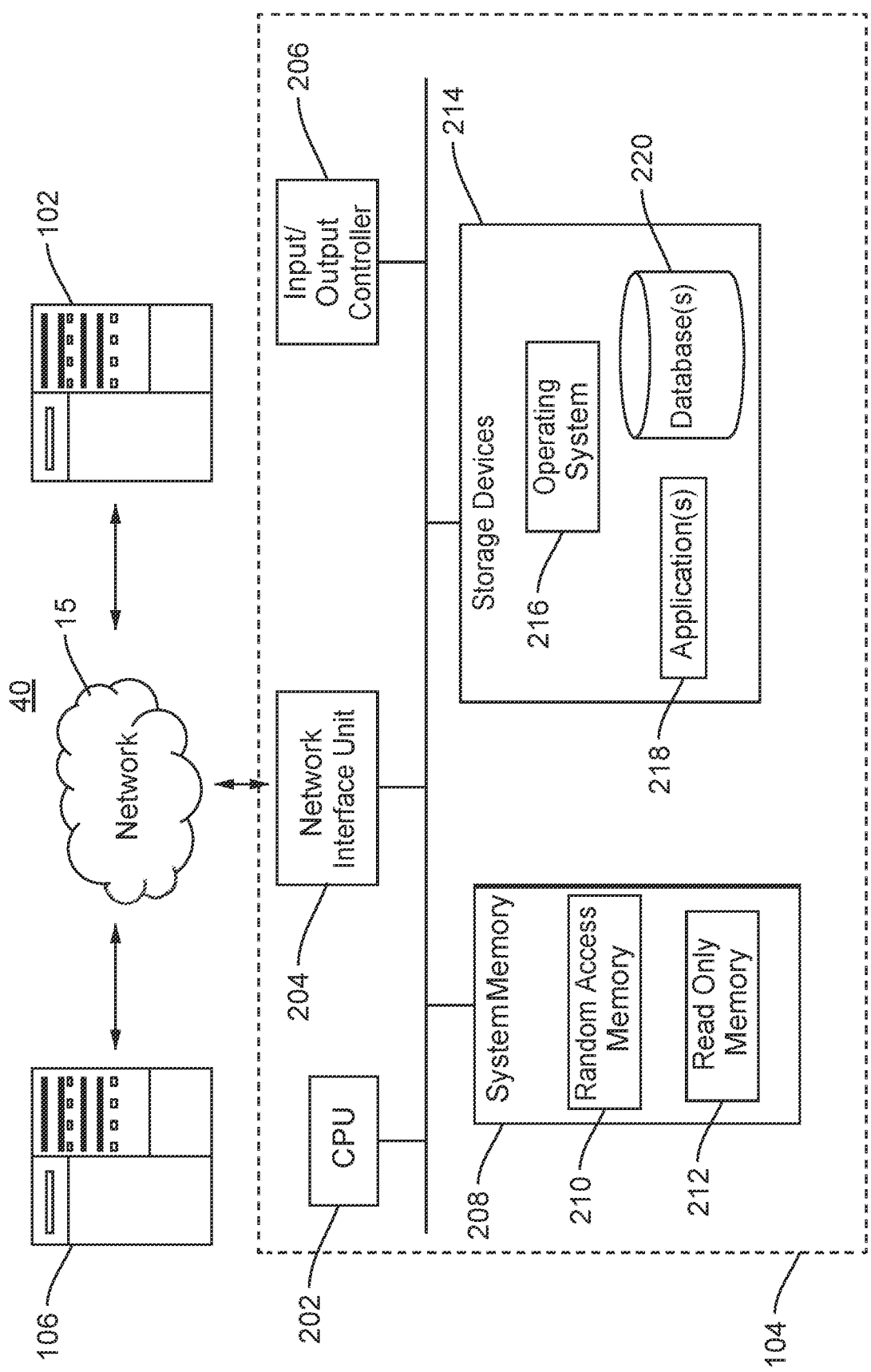
FIG. 2A illustrates a block diagram of the plan management platform for implementing the disclosed processes according to the disclosed embodiments.

FIG. 2A depicts a block diagram of plan management platform 40 for implementing the disclosed processes according to the disclosed embodiments. Platform 40 includes a network interface unit 204, an input/output controller 206, system memory 208, and one or more data storage devices 214. Data storage device 214 may correspond to storage device 43 shown in FIG. 1. System memory 208 includes at least one read-only memory (ROM) 212 and random access memory (RAM) 210. All of these elements are in communication with central processing unit (CPU) 202 to facilitate the operation of platform 40.

Platform 40 may be a standalone computer, or, alternatively, the functions of platform 40 may be distributed across multiple computer systems and architectures. Platform 40 may be configured to perform some or all of the content processing, predictive model processing, business logic processing, and plan management processing. These functions may be distributed across multiple devices within system 10. In some embodiments, platform 40 is connected via network 15 to other servers or systems within system 10. These may be shown as servers 102 and 106.

CPU 202 includes a processor, such as one or more microprocessors. CPU 202 also may include one or more supplementary co-processors such as math co-processors for offloading workload from CPU 202. CPU 202 is in communication with network interface unit 204 and input/output controller 206, through which CPU communicates with other devices such as other servers, user terminals, devices, and the like. Network interface unit 204 or input/output controller 206 may include multiple communication channels for simultaneous communication with other processors, servers, devices, and the like. Devices in communication with each other might not continually transmit to each other. For example, such devices need only transmit to each other as necessary.

CPU 202 also is in communication with data storage device 214. Data storage device 214 may include an appropriate combination of magnetic, optical, or semiconductor memory, and may include, for example, RAM, ROM, flash drive, an optical disc, and the like. CPU 202 and data storage device 214 each may be located within a single computer or other computing device or connected to each other by a communication medium, such as a USB port, a serial port cable, a coaxial cable, an Ethernet cable, a telephone line, a radio frequency transceiver or other similar wireless or wired medium or combination of the foregoing. For example, CPU 202 may be connected to data storage device 214 via network interface unit 204.

CPU 202 may be configured to perform one or more particular processing functions. For example, platform 40 may be configured as a content processor. The content processor retrieves external data from sources on the Internet and databases 102 and 106. The content processor also accesses data sources and extracts data for predictive model processing. The content processor may extract and manipulate data from text, images, or other formats delivered through web formats and applications. Platform 40 also may be configured as a predictive model processor. The predictive model processor receives input from the content processor to determine one or more recommended results to manage plans for consumers.

Data storage device 214 may store an operating system 216 for platform 40, one or more applications 218 (such as computer program code or a computer program product) adapted to direct CPU 202 in accordance with the embodiments disclosed below. One or more databases 220 may be adapted to store information that may be utilized to store information required by platform 40. Operating system 216 or applications 218 may be stored in a compressed, an uncompiled, or an encrypted format, and may include computer program code. The instructions of the programs and applications may be read into a main memory of the processor from a computer-readable medium other than data storage device 214, such as from ROM 212 or RAM 210. While execution of sequences of instructions in the program causes CPU 202 to perform the processes disclosed herein, hardwired circuitry may be used in place of, or in combination with, software instructions for implementation of the disclosed processes.

Figure 2B:
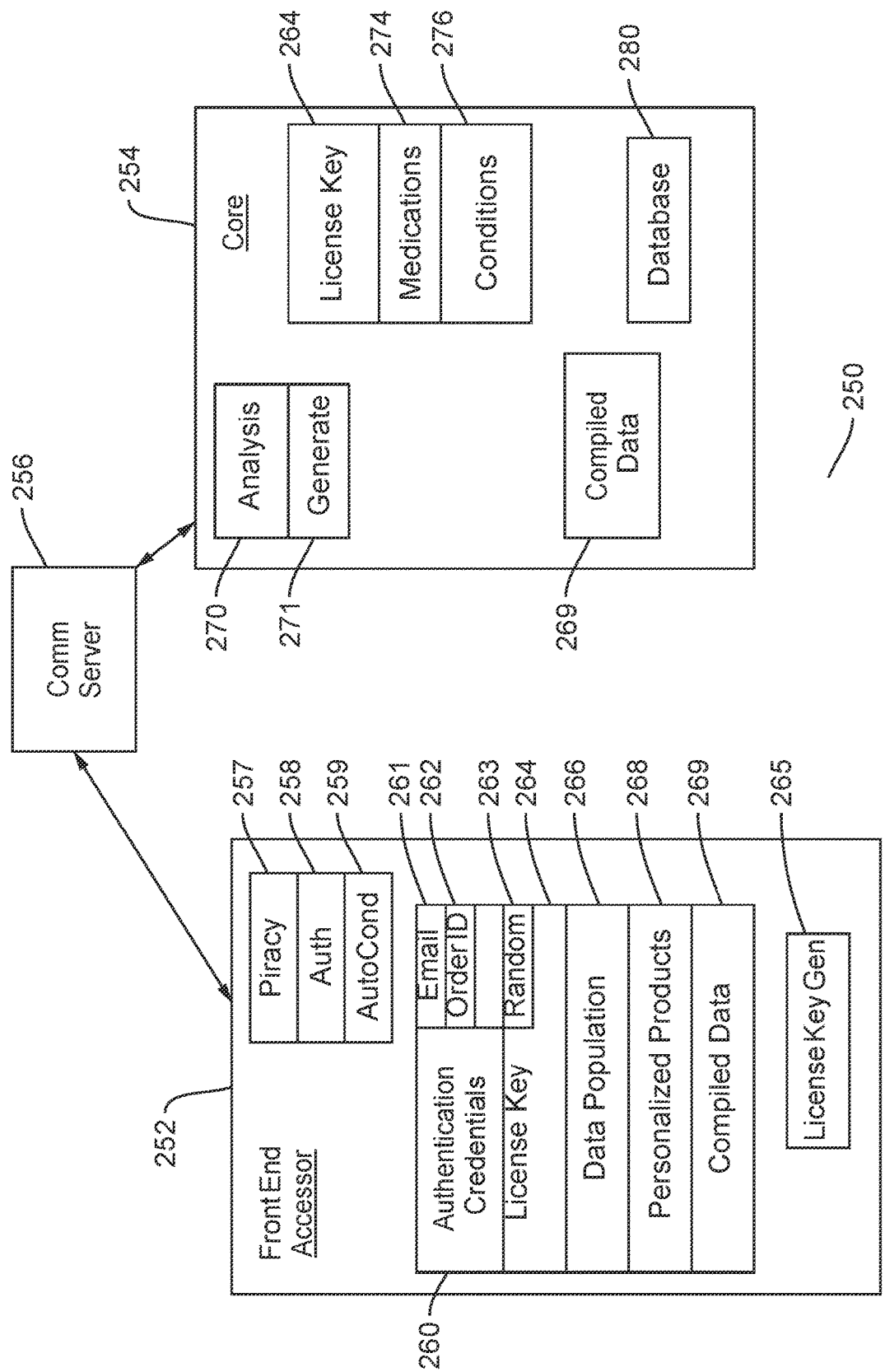
FIG. 2B illustrates a block diagram of a system to process a plurality of plans using a front end accessor and a core according to the disclosed embodiments.

FIG. 2B depicts a block diagram of a system 250 to process a plurality of plans using a front end accessor 252 and a core 254 according to the disclosed embodiments. System 250 also includes communication server 256. Communication server 256 may open communication ports with front end accessor 252 and core 254 so that these components do not exchange information and data directly with each other. Communication server 256 also may perform validation or authentication actions on communications between front end accessor 252 and core 254. In some embodiments, server 256 may reside with front end accessor 252 or core 254.

FIG. 2B shows components and data structures applicable to front end accessor 252 and core 254. Front end accessor 252 executes on the "front end" or with the agent or seller at their machine. Front end accessor 252 may be an application that collects, processes, and compiles data according to the disclosed embodiments. This data may be presented to core 254 for further processing and analysis. Core 254 may be a database that requires authentication before allowing access therein. The components and data structures for front end accessor 252 and core 254 are shown for illustrative purposes. Additional components and data structures may be implemented according to the disclosed embodiments.

Front end accessor 252 may be located on device 35 for an agent or seller of plans, such as health plans, that include a large amount of data and conditions applicable to each plan. Front end accessor 252 may be implemented with a graphical user interface to display and receive input at device 35. Front end accessor 252 executes as its own program such that instructions executable on a processor configures device 35 into a special purpose machine to perform the functionality disclosed below.

Front end accessor 252 may include piracy module 257 that executes to prevent pirating of the software associated with front end accessor 252 as well as access to core 254. Authentication module 258 executes to authenticate a user of front end accessor 252 as well as validate credentials of the user to access core 254. Autocond migration module 259 may execute the automatic condition migration processes disclosed in greater detail below.

Front end accessor 252 also includes data structures that used to perform the processes disclosed below. Authentication credentials 260 may be the data needed to authenticate the usage of front end accessor 252. This data may include user email 261 and order identification 262. Front end accessor 252 also stores license key 264, which is used to access and provide data to core 254. Random number string 263 may be added to license key 264. License key 264 may execute the license key generation module 265. Data population 266 may represent the data provided to front end accessor 252 from core 254, such as medication and condition data. Personalized products and plans 268 may be product and plan data selected or created for use by front end accessor 252.

Core 254, as disclosed above, may be a database. Preferably, core 254 is a processing engine with an encrypted database component 280 that is brought online when needed by front end accessor 252. Even though it may include database 280, core 254 may include call functions that cause processes to be executed when data is being accessed. These features are disclosed in greater detail below. Core 254 may include analysis module to perform the processing and analysis of data compiled and sent by front end accessor 252 to select the best plans for a potential customer. Generate module 271 may be executed to generate the database for core 254. Core 254 also may include license key 264 for front end accessor 252 when activated. It also includes medication data structures 274, which includes all the known data of medications applicable to all the plans as well as condition data structures 276 for all applicable conditions. Data structures 274 and 276 include large amounts of data points.

Figure 3:
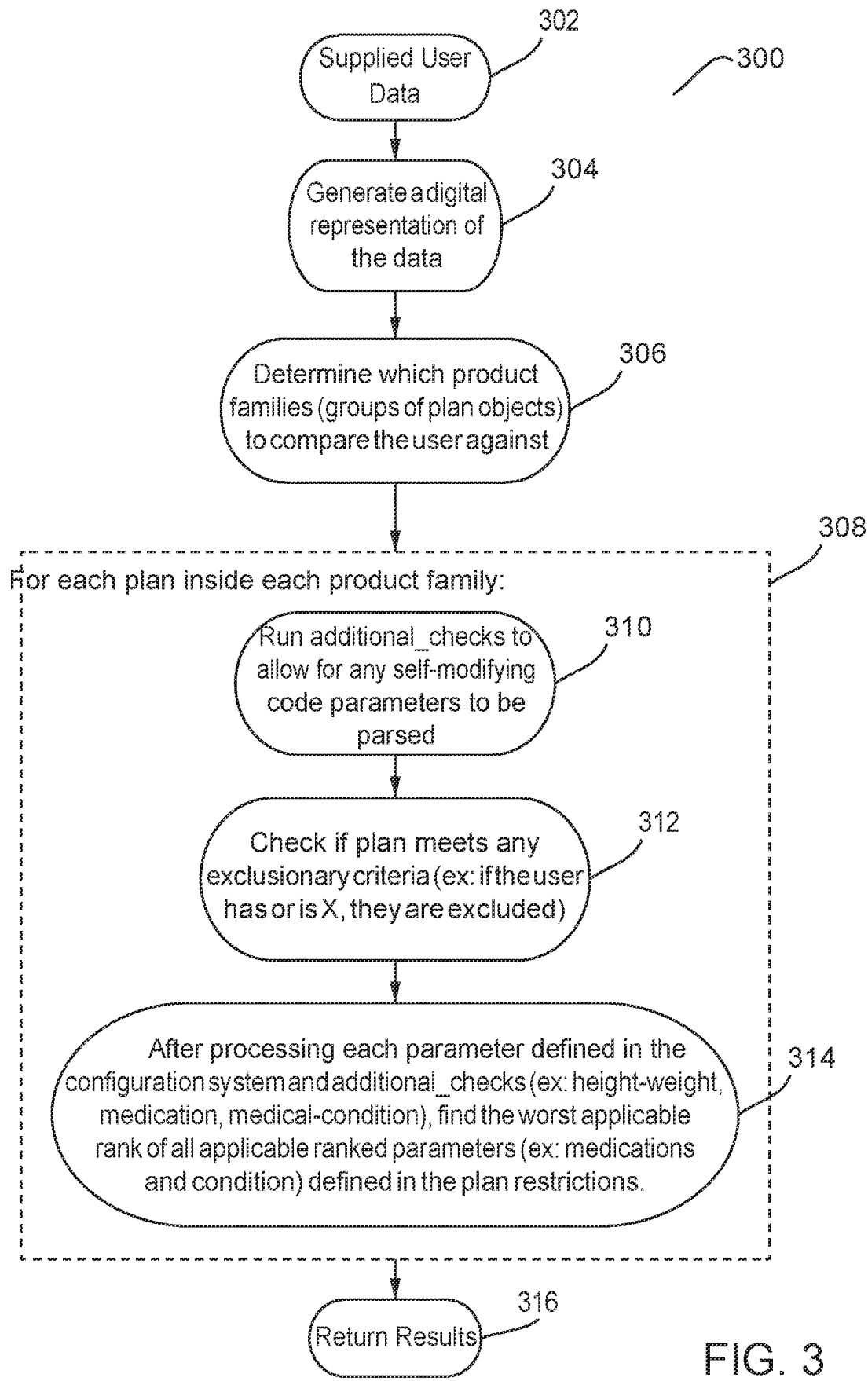
FIG. 3 illustrates a flowchart for managing plans using the platform according to the disclosed embodiments.

FIG. 3 depicts a flowchart 300 for managing plans using platform 40 according to the disclosed embodiments. Flowchart 300 may be implemented by platform 40 using data stored in servers 102 and 106 as well as collected over network 15. Step 302 executes by taking user data supplied via application 218 or via network 15 or other input/controllers 206. User data may include information that can be placed into objects of data such as name, age, sex, medications, height, weight, and the like. It also may include information such as hospital or doctor visits. Thus, user data should pertain the plans being managed and processed for the consumers.

Step 304 executes by generating a digital representation of the user data. The data is modeled in the software, or application 218, in a logical manner. The modeled data may be stored on platform 40 in database 220. Step 306 executes by determining which plan objects to compare against the user. In other words, certain plan objects have data that may be used to compare against data for the user. Step 306 may omit certain plans or product families from processing based around personalized products 268. Step 306 may assign different properties to the consumer, or actually the model of the person represented in the data. The properties may relate to the plan objects. This step may include analyzing a large amount of disparate data. In other words, not all user data is in a common format or in a readable form for platform 40. Some data may be digital, as stored on computer, while other data may be in a graphic form, such as a PDF of a scanned document. Platform 40 pulls the different user data need for the disclosed embodiments and uses it to determine the appropriate plan objects.

Step 308 executes by finding the right plan in a product family for each group of plan objects. Step 308 may be performed using steps 310-318 and may be repeated for each plan object staged for analysis in step 306. Step 310 executes by running or conducting additional checks to allow for any self-modifying code parameters to be parsed. Parsed user data maps all the data to the right location or to the right object. In this instance, the instructions can execute commands in the database to run the additional checks. The disclosed embodiments can execute core functions from the database assuming that functionality exists in core 254 or platform 40. Step 310 may take different parameters and modify virtual parameters by marking them in the database or modification algorithm. This step also may define exclusions, plan level, or product family.

Step 312 executes by determining if a plan meets any exclusionary criterion. For example, if the user has or is X, then that user is excluded from using the plan. "X" may pertain to a parameter found in the objects of the user data. Using another example, if X is age, then a plan only for senior citizens would be excluded from being recommended to someone being 23 years old. Some exclusions are global in nature so that many plans may be excluded early in this step such that processing requirements are reduced.

Step 314 executes by processing each parameter defined in the configuration system and additional checks being performed to determine the worst rank of applicable restrictions. For example, height, weight, medication, medical conditions may be checks used to determine whether a plan fits. The parameters within the user data are used to compare or match against the information for the user. Step 316 executes by returning the results of finding the right plan in the product family set forth by step 310.

Figure 4:
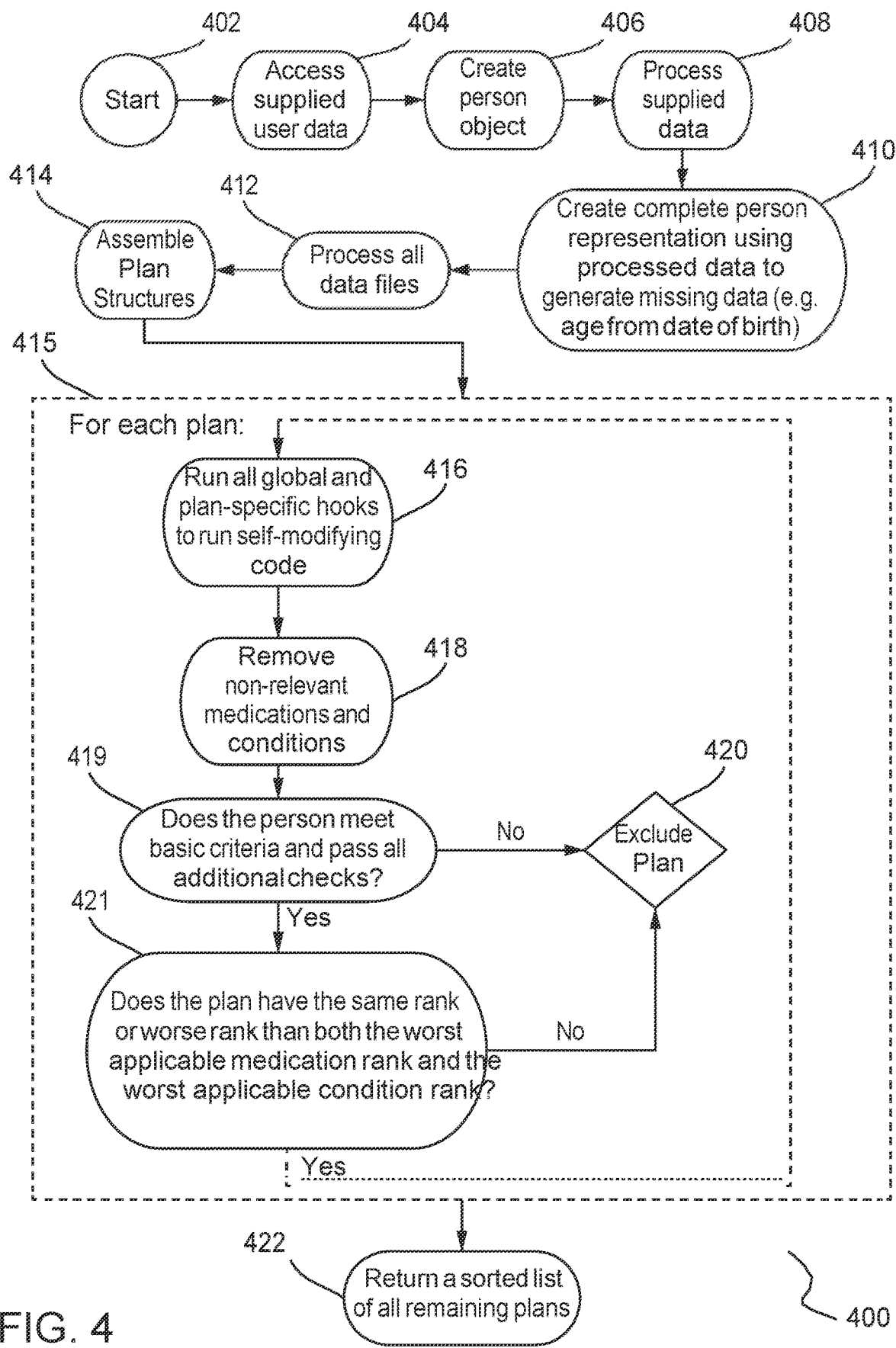
FIG. 4 illustrates a flowchart for analyzing a plurality of plans using the platform according to the disclosed embodiments.

FIG. 4 depicts a flowchart 400 for analyzing a plurality of plans using platform 40 according to the disclosed embodiments. Flowchart 400 may disclose an alternative process to manage a plurality of plans, such as disclosed by flowchart 300. For example, the end result provided by step 422 may be returning a sorted list of plans, which is similar to step 316 disclosed above. Flowchart 400, however, may differ in how it accomplishes this result.

Step 402 executes by starting flowchart 400. Step 404 executes by accessing the supplied user data. Referring back to FIG. 2, user data may be stored at servers 102 and 106. As disclosed below, the user data for the customer may be provided to core 254. Alternatively, user data may be available on platform 40 in database 220. Preferably, the database is a text file which allows for encryption, integrity, and security. The user data embodied in the database may be sent to platform 40 if it is executing application 218 to implement the disclosed embodiments. The user data may be accessed via command-line switches or via an input file.

Step 406 executes by creating a person object. Preferably, the person object is created from parsed customer data obtained by the user. Thus, step 408 executes by processing the supplied data by loading the pre-existing data structures into memory supplied from the database in core 254 or processing plan files supplied from the database in core 254. Slurping may refer to reading files into memory. Step 410 executes by creating a complete person representation using the processed customer data generating missing data. For example, if a person's date of birth is provided, then the age of the person is calculated. Weight may be converted from pounds to kilograms.

Step 412 executes by processing all data files. Step 414 executes by assembling plan data structures. The disclosed embodiments read in all data files from the appropriate database and assembles plan structures while removing any data that does not apply. Steps 412 and 414 also may read in all plans being considered. Steps 412 and 414 may be omitted if the data structures are loaded directly into memory from the database in core 254.

Step 415 includes sub steps 416-421 which seek to remove plans for which the person does not qualify via the parameters within the user data. The available plans are updated using this process. Step 416 executes by running all global and plan-specific hooks or checks to run self-modifying code. In other words, step 416 runs global and plan-specific additional checks in case there is a self-modifying check, such as some item that prevents height or weight from being examined. The database may hook back to core 254 to force the core to run code that it would not normally execute.

Step 418 executes by removing non-applicable restrictions from the plan data structures. For example, step 418 may remove restrictions on cancer if, after step 408, the person doesn't have cancer or any sub-type of cancer. Step 419 determines if the person meets the basic requirements for the plan, including, but not limited to height & weight requirements and plan-specific and product-specific additional checks. If step 419 is no, then step 420 executes by excluding the plan being evaluated. If it's a yes, then step 421 executes.

Step 421 executes by determining the worst rank of all remaining components, namely the medications and conditions. If the current plan's rank is better than the worst rank, step 420 executes by excluding the plan. If the current plan's rank equal or worse than the current worst rank, the plan is left untouched and the system repeats step 415 for each remaining plan. After all plans have been evaluated, step 422 executes to return a sorted list of the best ranking plan for each requested product.

Figure 5:
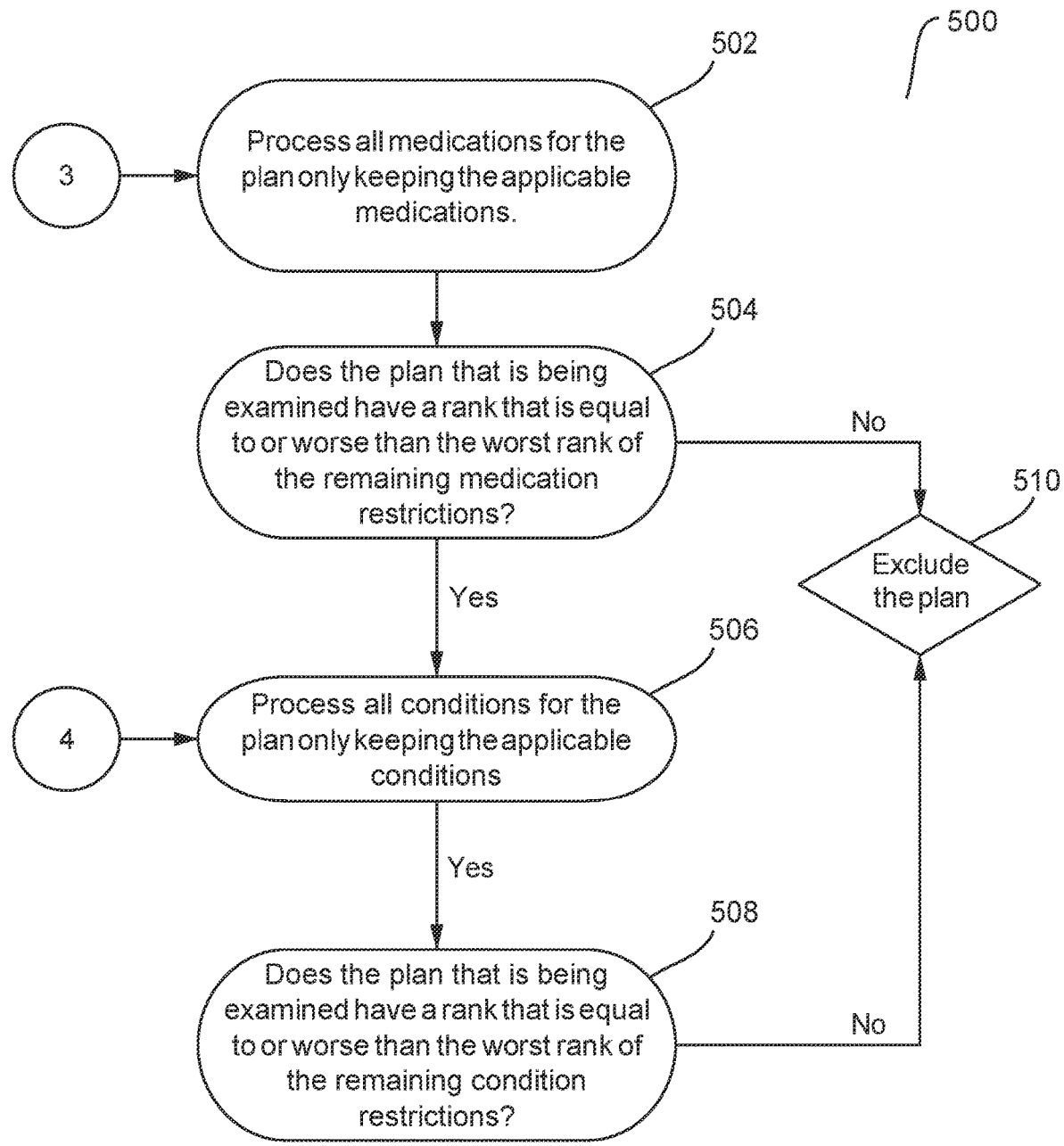
FIG. 5 illustrates a flowchart for determining whether a person representation meets the criterion of a plan according to the disclosed embodiments.
Figure 6:
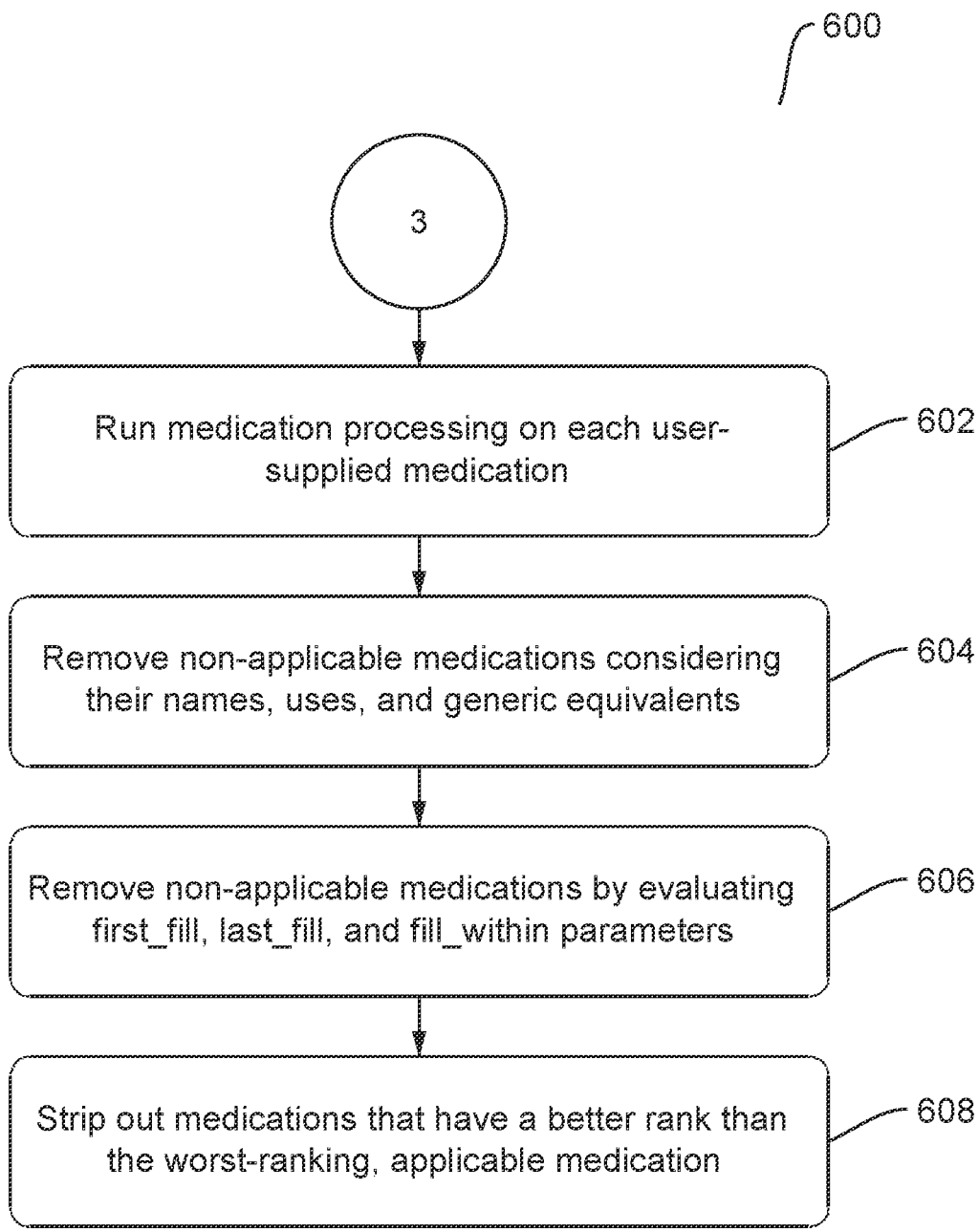
FIG. 6 illustrates a flowchart for processing medications in determining whether a person representation meets applicable criteria according to the disclosed embodiments.

FIG. 5 depicts a flowchart 500 for determining whether a person representation meets the criterion of a plan according to the disclosed embodiments. Flowchart 500 may correspond to sub-step 418 in FIG. 4. Step 502 executes by processing all medications for the carrier only keeping the applicable medications with the worst rank. This step is disclosed in greater detail by FIG. 6. FIG. 6 depicts a flowchart 600 for processing medications in determining whether a person representation meets application criteria according to the disclosed embodiments.

Thus, step 602 executes by running medication processing on each user-supplied medication. Step 604 executes by removing non-applicable medications considering names, uses, and generic equivalents. Step 606 executes by removing non-applicable medications by evaluating first_fill, last_fill, and fill_within parameters. These parameters may correspond to the first time a prescription for the medication was filled, the last time it was filled, and a period for the medication to be provided. Fill_within may be omitted from this processing if it overlaps with the last_fill parameter, however it may serve as a synonym to the last_fill parameter. Step 608 executes by removing medications that have a better rank than the worst-ranking, applicable medication. The medications then may be provided back to flowchart 500.

For example, for each medication object in the person representation, the disclosed embodiments check to see if it abides by a defined medication restrictions. Additional processing is executed on the medication, such as date translation, generic population, and the like. This may be information obtained from provided data that need to be converted or calculated. The disclosed process may check for restrictions of the first_fill parameter for the medication. If the person representation indicates that the user takes the medication outside the window provided by the first_fill restriction, then the person representation does not meet the medication requirements for a particular plan. If the medication either is outside of the first_fill parameter window or the plan does not pose a restriction on the first_fill parameter, then the disclosed process checks if the plan restricts the fill_within or last_fill parameters and if the person representation includes data that the medication is taken within the window provided by the fill_within and last_fill parameter, such as determining whether the medication has been filled in the last two months. If the determination that medication represented in the person object matches the defined fill_within or last_fill parameters or if there are no restrictions on first_fill, fill_within, or last_fill, then the person representation meets the medication requirements for the plan. Otherwise, it does not and the restriction does not apply. This is repeated for each medication represented inside of the person representation to find a plan that meets all of the medication criteria. The goal of this process is to restrict plans to the best ranking plan that fits all of the applicable medication restrictions. For example, if a plan restricts a medication X requiring that it was filled within the last 4 months and it was actually last filled 6 months ago, the restriction defined by this plan does not apply and the process will continue to step 504.

Figure 7:
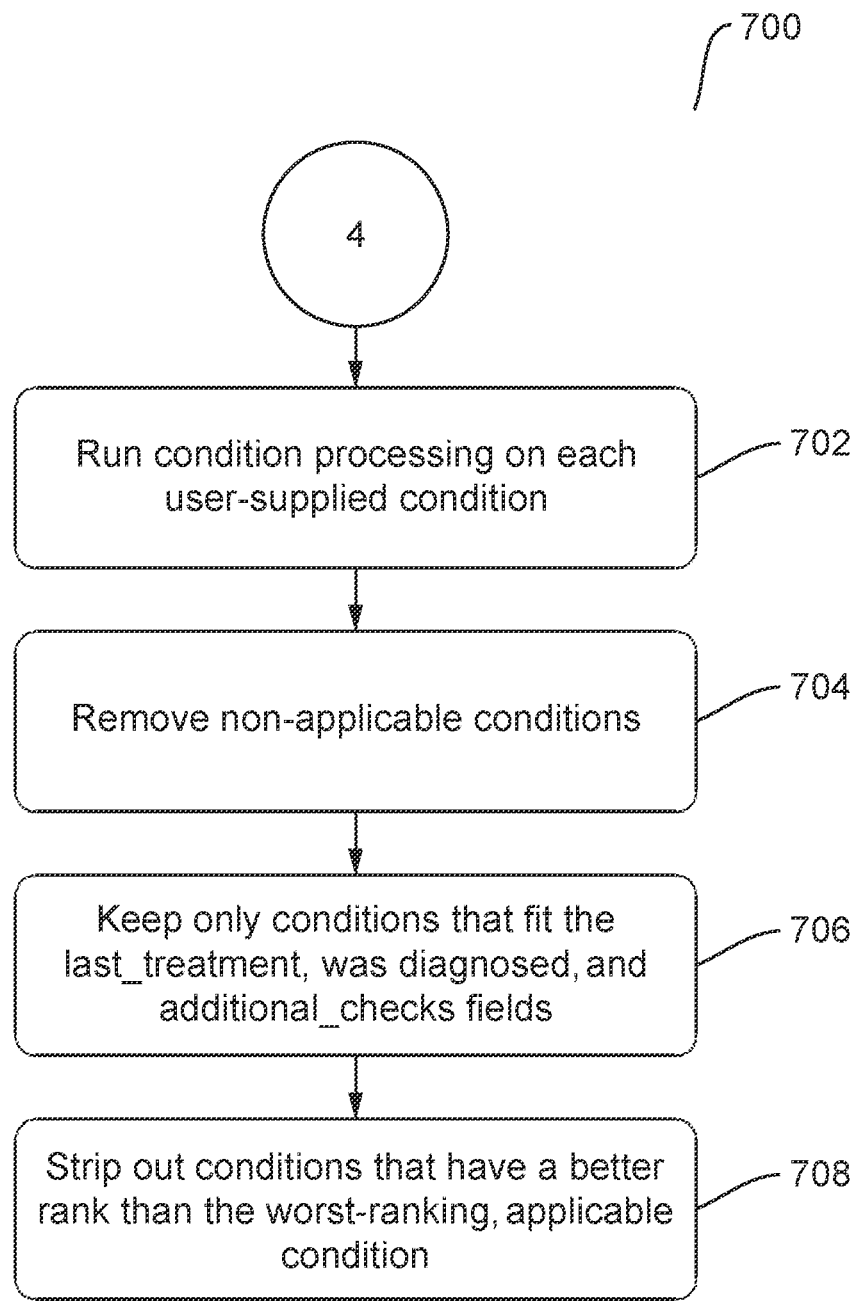
FIG. 7 illustrates a flowchart for processing conditions in determining whether a person representation meets applicable criteria according to the disclosed embodiments.

Returning back to flowchart 500, step 504 determines if all medications fit restrictions defined by the examined plan and the examined plan has a rank equal to or worse than the worst rank of the medications. If not, it excludes the plan 510 and moves to the next for that product family, or, if there are no further unexamined plans for the product family, either moves onto the next product family 308, or returns results 316. Step 506 executes by processing all conditions for the product, only keeping the application conditions with the worst rank. This step is disclosed in greater detail by FIG. 7. FIG. 7 depicts a flowchart 700 for processing conditions in determining whether a person representation meets application criteria according to the disclosed embodiments. Flowchart 700 may remove all conditions for each carrier and identify which ones are applicable to the user, or person representation.

Step 702 executes by running condition processing on each user-supplied condition. For example, the processing may convert date formats. Step 704 executes by removing non-applicable conditions from the list of conditions. The parameters may pertain to a variety of conditions but not every condition has a parameter provided by the user supplied data. If a person does not have diabetes, then conditions for diabetes need not to be checked. Step 706 executes by keeping only the conditions that fit the last_treatment, was_diagnosed, and additional_checks fields or parameters. Step 708 executes by removing conditions that have a better rank than the worst-ranking, applicable condition. The conditions may be provided back to flowchart 500.

For example, the condition may be checked to determine if it was treated within a restricted window, if a restricted window is defined. The condition also may be checked to determine if it was diagnosed within a restricted window, if a restricted window is defined. The condition may be checked to determine if it came about during a restricted age-of-onset window, if one is defined. Cross-plan conditions are resolved. In other words, one condition may have multiple applicable plan options, so the worst ranking applicable option is chosen.

Returning back to flowchart 500, step 508 executes by checking that the plan that is being examined has a rank that is equal or worse than the rank of the conditions. Step 508 may remove all plans that have a better rank than the worst rank in the conditions list. For example, if the worst rank in the conditions list is a 3, then remove all ranks better than 3. The list and rankings of the plans may be returned to flowchart 400.

FIGS. 8-17 disclose additional embodiments of the process to use compiled data to determine the best plans to present to a customer, wherein the plans relate to a population having specific data, such as medicine, and conditions. FIGS. 8-17 refer to FIGS. 1, 2A, and 2B for illustrative purposes.

Figure 8:
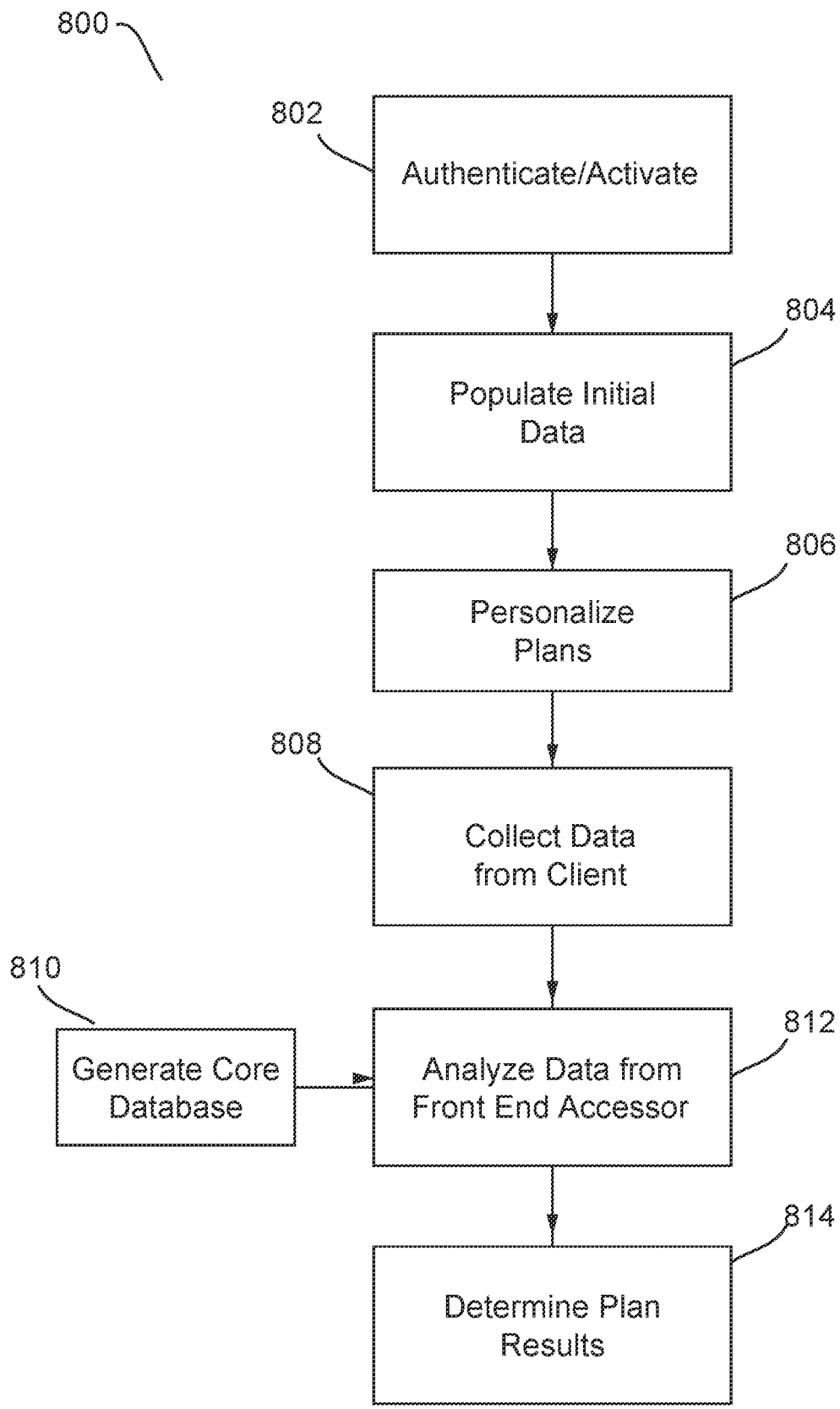
FIG. 8 illustrates a flowchart for a front end accessor for an application of the disclosed embodiments.

FIG. 8 depicts a flowchart 800 for processing a plurality of plans having data and conditions for a population according to the disclosed embodiments. Flowchart 800 may include the steps used to activate and validate the application for front end accessor 252 as well as obtaining data from core 254. Flowchart 800 also includes the steps to analyze data to provide recommended plans to an agent or seller for a specific customer.

Step 802 executes by authenticating or activating the use of front end accessor 252 to propose plans to a customer. Mitigation of piracy of the associated software and data of the disclosed embodiments also is performed in this step. Step 802 also may generate license key 264 for front end accessor 252. Step 802 is disclosed in greater detail below in FIG. 9.

Figure 9:
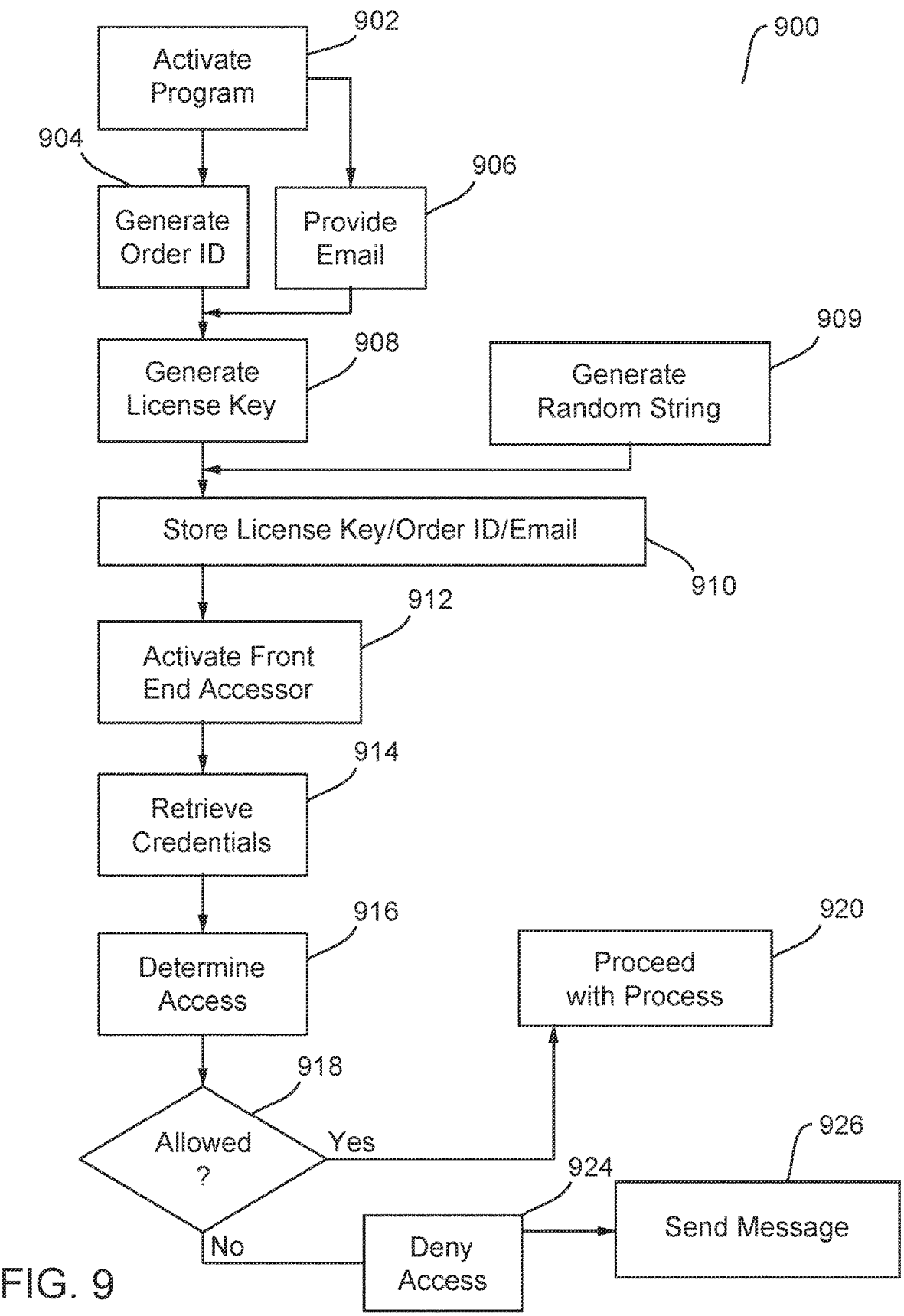
FIG. 9 illustrates a flowchart for authenticating or activating access to the front end accessor according to the disclosed embodiments.

FIG. 9 depicts a flowchart 900 for authenticating or activating access to front end accessor 252 according to the disclosed embodiments. The steps disclosed by flowchart 900 may be used to mitigate the threat of piracy of the disclosed software components and associated data. The target audience of the disclosed embodiments are not necessarily computer savvy. Agents may share software programs and access to databases on a regular basis by intentionally or unintentionally sharing credentials with other users. For example, an agent may provide his/her user name and password to a new agent to "get started" on providing plans to customers without the need for formal training or establishing separate credentials. Further, a business may only have access to a certain number of plans and does not want to pay to increase this number. The disclosed embodiments seek to mitigate these situations and prevent unauthorized or accidental access to licensed programs as well as sensitive data stored at core 254. The disclosed processes allow for activations of programs, such as front end accessor 252, without the user maintaining the secrecy of his/her credentials being relevant.

Step 902 executes by activating the program for front end accessor 252. The user may purchase a license or request someone to be added to a current license. The user may pay an associated license fee. Step 904 executes by generating an order identification 262. Order identification 262 may be a number or other characters generated by front end accessor 252 on its payment of license fee. Step 906 also executes at some point during steps 902 and 904 by the user providing his/her email address 261. These steps may be executed by opening the disclosed embodiments at a webpage to register for access to front end accessor 252.

Step 908 executes by generating license key 264. License key 264 is generated programmatically during the activation procedure and is stored in the user's software settings, as shown in FIG. 2B being stored with front end accessor 252. License key 264 is sent to front end accessor 252 during its application program interface (API) calls. It may use a 25 character sequence comprising of 5 check digits that allow for integrity checking. Front end accessor 252 checks to ensure that the license is valid using the check digits. This process may hinder piracy amongst agents and brokers using the disclosed embodiments.

Figure 10:
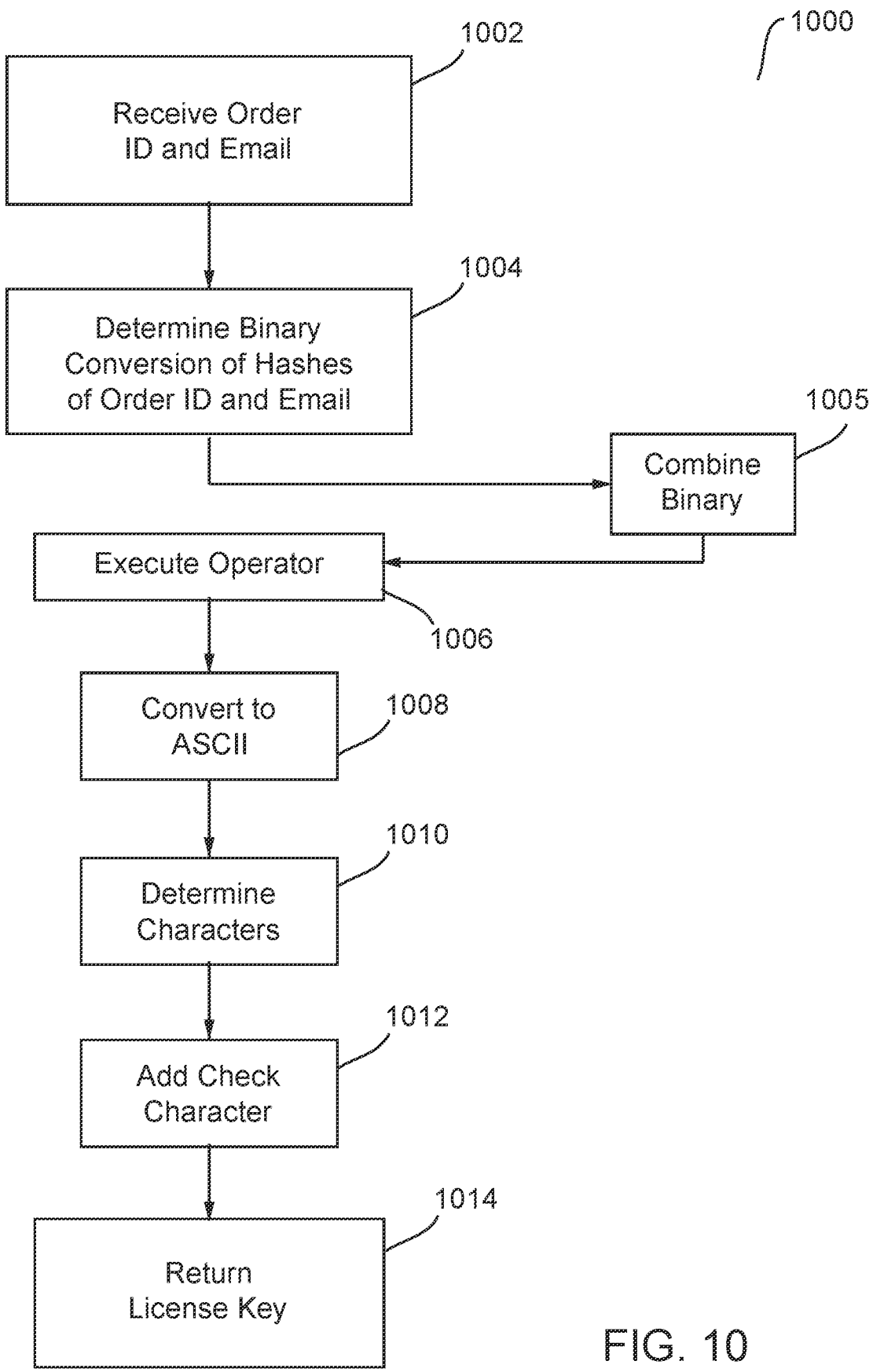
FIG. 10 illustrates a flowchart for generating a license key according to the disclosed embodiments.

FIG. 10 depicts flowchart 1000 for generating a license key 264 according to the disclosed embodiments. Flowchart 1000 may correspond to step 908 disclosed above. Step 1002 executes by receiving order identification 262 and email 261 as provided by the user. Step 1004 determines the binary conversion of the hashes of order identification 262 and email 261. Preferably, the hashes are sha512 hashes. Step 1005 executes by combining the binary of the two lists via concatenation.

Step 1006 executes by executing an operator on the current character and the next character. In some embodiments, an xor operator is run on the current character and the next character after evaluating the "or" and "and" of both binary characters, pushing the resultant character onto a list. Step 1008 executes by converting the new characters to American Standard Code for Information Interchange (ASCII) format. The disclosed embodiments may use a script executing at front end accessor 252 to convert the characters.

Step 1010 executes by determining a number for the converted characters and getting those characters according to the disclosed embodiments. For example, twenty (20) characters may be obtained starting with a predefined choice. Step 1012 executes by adding a check character at the end of every four (4) characters by summing the previous four (4) characters. The resulting five (5) character blocks results in license key 264 with the character blocks separated by a "-". Step 1014 executes by returning license key 264. License key 264 is stored at front end accessor 252.

Returning to flowchart 900, step 909 executes by generating a random string 263 to be included with license key 264. Random string 263 allows for multiple registrations of the same order id and email combination. Random string 263 may be a secret key that acts as a tracking agent for each device that registers into front end accessor 252. In other words, multiple devices 35 may use order id 904, email 906, and license key 264 as an agent moves around or uses different devices, such as a desktop, laptop, tablet, or smartphone. Random string 263 is checked during specific procedures and during the execution of regular queries. If random string 263 appears in the random string database table, then the disclosed embodiments know that the device has been activated before. If it does not then the disclosed embodiments know that is has not. When opening a fresh installation of the offline software, it generates a new random string. For online activation, it generates a random string if one does not exist in the stored data.

When dealing with multi-activation licenses, an intermediate procedure may be implemented that integrate random strings until the maximum activations have been reached. The intermediate procedure is a quasi-quantum mechanical algorithm that invokes being able to determine which random strings are intended to be active. There is an unknown trait to multi-license activations. Is the license's random string associated to a particular activation? If so, how can the disclosed embodiments tell the difference between a re-register due to a new device or due to piracy?

Each random string is assigned an active status, such as 0 for inactive, 1 for active, and 2 for unknown. If someone has an active random string and then activates on a new computer, then all random strings marked active become unknown, except the random string that was just created on the new computer, which is marked active, or 1. If the number of active random strings is the same as the maximum activations on the license, then all the unknowns are known to be inactive. Otherwise, the disclosed embodiments need to wait for the user to activate another one of their unknown random strings, which will then be moved to active.

Step 910 executes by storing license key 264, order identification 262, and email address 261 at front end accessor 252. These credentials may be stored in the settings of the program executing on device 35. For example, license key 264 may be stored in a browser along with other information, as disclosed below. Random string 263 also may be stored, if one was generated in step 909.

Step 912 executes by activating front end accessor 252. A user may activate to use the disclosed embodiments to analyze and propose plans to a customer. Front end accessor 252, however, must determine if access is allowed from the device executing the application. Step 914 executes by retrieving the credentials stored in the settings of front end accessor 252, such as email address 261, order identification 262, license key 264, and random string 263.

Step 916 executes by determining whether front end accessor 252, by activation 912, has access to the data and other program functions of the disclosed embodiments. During a query run, the disclosed embodiments check to see if random string 263 is the most recent string for a particular order identification 262 with the intermediate procedure disclosed above in step 909 being run after each iteration. As a result of the check, access may be allowed, as disclosed below.

Figure 11:
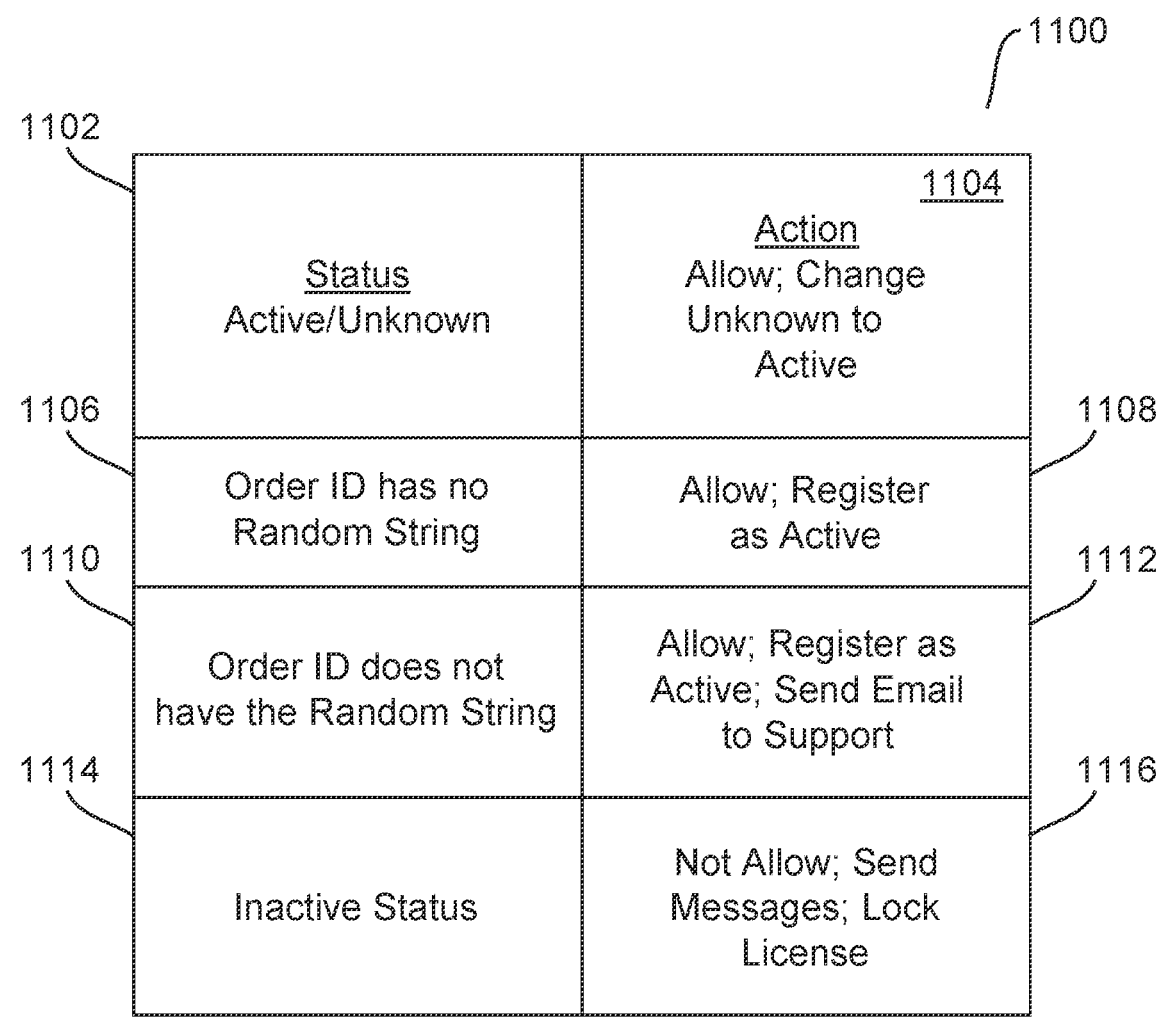
FIG. 11 illustrates a table of the status and actions to be taken based on the random string associated with a license key according to the disclosed embodiments.

Step 918 executes by determining whether a "gate," such as piracy module 257 or authentication module 258, will allow the query to pass through to activate front end accessor 252. Reference may be made to FIG. 11, which depicts a table 1100 of the status and actions to be taken based on random string 263 of license key 264 according to the disclosed embodiments. Based on the results of step 916, a status is determined with a resulting action being taken.

Status 1102 represents that the active status as active or unknown. Using the intermediate procedure designations disclosed above, the active status may be a 1 or a 2, which corresponds to active or unknown, respectively. Status 1102 results in action 1104. Action 1104 indicates that the gate will allow the query to pass through. Further, an unknown status may be changed to active, or changed from a 2 to a 1, for the license key and random string for the device hosting front end accessor 252. It may mark unknown status strings as inactive, or 0, if the maximum number of simultaneous activations is reached.

Status 1106 represents that order identification 262 does not have a random string associated with it. Action 1108 is taken that allows the query to pass through. The disclosed embodiments will register the random string with a status of active, or 1.

Status 1110 represents that order identification 262 was provided without a random string. Action 1112 is taken that allows the query to pass through and registering the random string with a status of active, or 1. It also may run the intermediate procedure disclosed above. The disclosed embodiments also will send an email to support staff indicating that a license corruption may have occurred along with applicable credentials, such the email, order identification, and random string. This feature will allow support to manually deal with this case of potential piracy even though the gate allows the query to pass through.

Statuses 1102, 1106, and 1110 correspond to a yes condition for step 918. As such, step 920 executes by proceeding with the disclosed processes in flowchart 800. Status 1114 corresponds to a no condition for step 918. Status 1114 represents a known random string having an inactive status, or 0. This may mean that the user has an active subscription on another device. If the user has not reached their maximum activations, the random string will not have an inactivate status, or 0. Instead the status will either be active or unknown, 1 or 2 respectively. Action 1116 is taken that does not allow the query to pass through. An appropriate message may be sent as well as displayed on device 35. The following actions may be taken with this respect.

At device 35, a message may be displayed that the maximum allowed activations for the license has been reached. The user should deactivate front end accessor 252 on another device before activating it on the current device. Further, the license may be locked temporarily and will automatically unlock after a specified period of time, such as four (4) hours. This allows use of front end accessor 252 on another currently active device without issue, if the attempted piracy is accidental and will prevent a pirated license from being activated. An email is sent to support, as disclosed in action 1112. Further, an email may be sent to the license holder that someone tried to use their license without proper credentials and that access is temporarily locked. A text message also may be sent to this effect.

Thus, referring back to flowchart 900, if step 918 is no, then step 924 executes by denying access through front end accessor 252 at device 35. Step 926 executes by sending the appropriate emails and messages as disclosed above.

Now that use of front end accessor 252 on the particular device is validated and any piracy concerns dealt with, the disclosed embodiments return to flowchart 800. Step 804 executes by populating front end accessor 252 with the initial data to execute the disclosed processes. Communication server 256 may receive license key 264 to obtain the initial data from core 254. Communication server 256 then provides the data back to front end accessor 252. This feature provides a layer of separation between front end accessor 252 and core 254. The initial data from core 254 comprises medications data structure 274 and conditions data structure 276. Access is allowed only if authenticated. The initial data may be large. For example, medications data structure 274 may include data stored for 15,000 medications.

Step 806 executes by personalizing the plans by the user. The user may go into settings to review products, also known as product families, that he/she is authorized to sell. Each product usually has several plans. The disclosed embodiments try to compare apples to apples in this process. Data on the various products and plans are brought to front end accessor 252. For example, a carrier may be cited along with applicable products having at least two plans each. The product may have a name. The plan information pertains to the type of coverage.

At least two plans are associated with each product. The two plans may be no coverage or exclude and at least a basic plan. Other plans may be available for each product as different coverages are outlined for each plan. The user also may set the personalization to a default state. Step 806 allows the user to select those products and plans that he/she is allowed or interested in selling. There is no need to provide information on products or plans that have no interest or applicability to the user.

Figure 12:
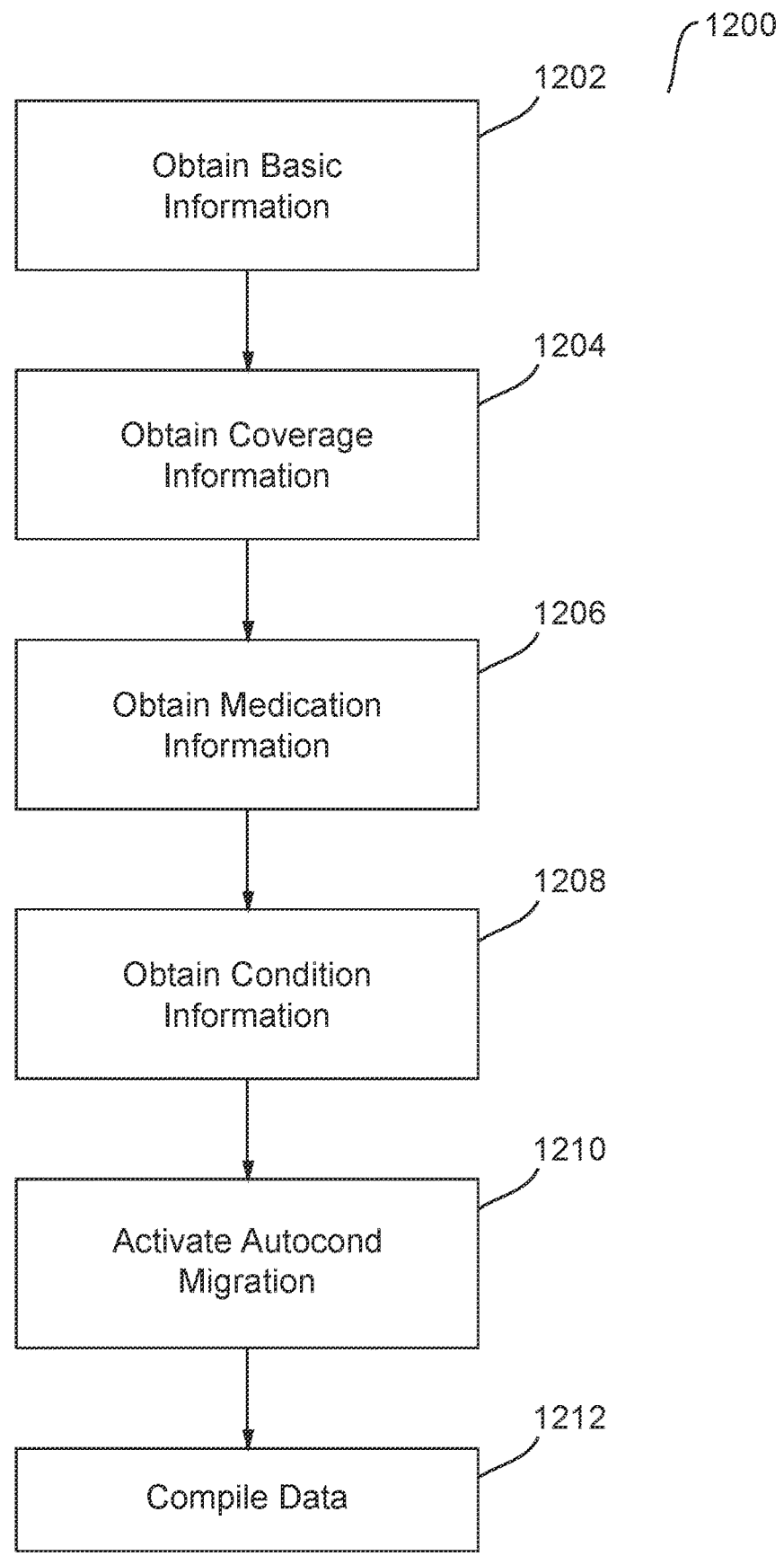
FIG. 12 illustrates a flowchart for collecting data for a customer according to the disclosed embodiments.

Step 808 executes by collecting data from the potential client or customer. This step is disclosed in greater detail by flowchart 1200. FIG. 12 depicts a flowchart 1200 for collecting data for a customer according to the disclosed embodiments. Step 1202 executes by obtaining basic information from the customer, such as height, weight, age, sex, and the like. Step 1204 executes by obtaining coverage information from the customer. For example, the customer may indicate how much or the type of coverage he/she is willing to purchase.

Step 1206 executes by obtaining medication information from the customer. The disclosed embodiments allow for the collection of medication information and the display of that information. The user, or agent, can also view known uses of the medication. The uses are the summation of all of the restricted uses in the plans and is not meant to be exhaustive. The known uses may come from the initial data provided in step 804 disclosed above. Other information collected for each medication should include the first fill and last fill of the prescription.

Step 1208 executes by obtaining condition information from the customer. This step allows for the collection of condition information and the display of that information. The user also may view known diagnostic criteria of the condition. These criteria are the summation of all of the diagnostic criteria given on applications and underwriting guides in the plans' definitions and is not meant to be exhaustive.

The information obtained in steps 1202-1208 may be performed in any order. The information displayed in the steps is meant to guide further questioning to the customer. For example, a customer may be on medication for so long that he/she cannot remember the initial diagnosis that led to the prescription. In some embodiments, listing of a medication will automatically add at least one condition to step 1208. First fill and last fill information may be used to populate data for the applicable condition.

Step 1210 executes by activating automatic condition, or autocond, migration. Step 1210 may activate in step 1208 when entering and addressing conditions for the customer. Autocond migration is the process in which the disclosed embodiments extrapolates conditions from data, like moving medication uses to the list of conditions and extrapolating dates from given data or adding additional conditions automatically. Autocond migration is disclosed herein as part of the front end processing but also may be performed in core 254. Autocond migration is important to get a more robust picture of the health of the customer by suggesting the agent inquire about additional, likely conditions.

Some conditions imply other conditions, especially when it comes to medical conditions. At front end accessor 252, autocond migration may prompt the user to clarify medical information with the customer. It also will determine or estimate some dates and conditions based on data provided above. For example, a customer may be prescribed oxygen. The customer indicates that it was prescribed for cancer. An autocond migration trigger will add cancer with the review indicator to the conditions list. An autocond trigger may also run to add oxygen, cancer (remission), and cancer (active) to the conditions list with the review indicator as well so that the user can discuss with their client which conditions are relevant, the dates of their diagnosis, treatment, and refining the types of their illnesses where applicable, such as narrowing cancer to cancer (lung). Potential conditions requiring oxygen, such as COPD or oxygen treatment, may be added with the relevant dates due to these prompts.

At core 254, autocond migration also may be used to apply condition restrictions of another condition to the customer, but those restrictions will not be added under the alias process, disclosed below. The criteria for autocond migration may commonly be when there is a condition that should inherit the properties of another condition, but does not meet the criteria for an alias. An alias is a categoric relationship defined as a parent and child relationship, where the child inherits properties of the parent, or a circular relationship where both properties are synonyms. If the user adds diabetic neuropathy, then core 254 will use autocond migration to add diabetes, diabetic complications, and neuropathy as autoconds of diabetic neuropathy. There may be global autoconds and local autoconds set forth in the additional requirements sections of each plan file as an additional check. If someone has diabetic neuropathy, then the disclosed embodiments should know that the customer inherits the same restrictions as diabetes but, technically, diabetes is not a more generalized version of diabetic neuropathy as they are not on the same branch of conditions, thus not a categoric relationship or synonym and, thus, not an alias. To apply the diabetes restrictions to the customer in order to exclude certain plans, the disclosed embodiments need to add the condition diabetes with the same properties as diabetic neuropathy.

Step 1212 executes by compiling the entered information and autocond migration data into compiled data structure 269. Compiled data structure 269 is then passed to core 254 for the further processing according to the disclosed embodiments. Additional features of this process may include searching. For condition names, the user can enter a partial string of characters into the name field. The disclosed embodiments, using front end accessor 252, then searches the list of conditions containing all characters and words to try and narrow down the options. If no option exists with all the search terms, then the disclosed embodiments searches for conditions containing any of the words in the search field. If the disclosed embodiments find only one match, then it places that match into the name field for the condition and removes focus to prevent additional keystrokes in the field by accident. This functions as autocomplete. If the user re-enters the name field, then an override flag is signaled that prevents autocompletion on this particular condition. The flag is reset when the condition window is closed.

Another feature may be a translation system used by front end accessor 252. The translation system is a key-value translation system where any data-focused text field translates user input into other input. The data-focused fields with the translation system enabled are medication name, medication use, and condition name. The translation system also may be used to fix typographical errors, such as CHOLESTERAL to CHOLESTEROL, deal with common abbreviations, such as HBP to HIGH BLOOD PRESSURE, and translate one condition name to another, such as HYPERTENSION to HIGH BLOOD PRESSURE. The disclosed translation system may work on individual words without having to rewrite the entire field.

At this instance, the focus of flowchart 800 moves from front end accessor 252 to core 254, or to back end processing of compiled data structure 269. Before the analysis of the compiled data can begin, core 254 must be generated or decrypted if already generated. Step 810 executes by generating core 254. This process is disclosed in greater detail by flowchart 1300.

Figure 13:
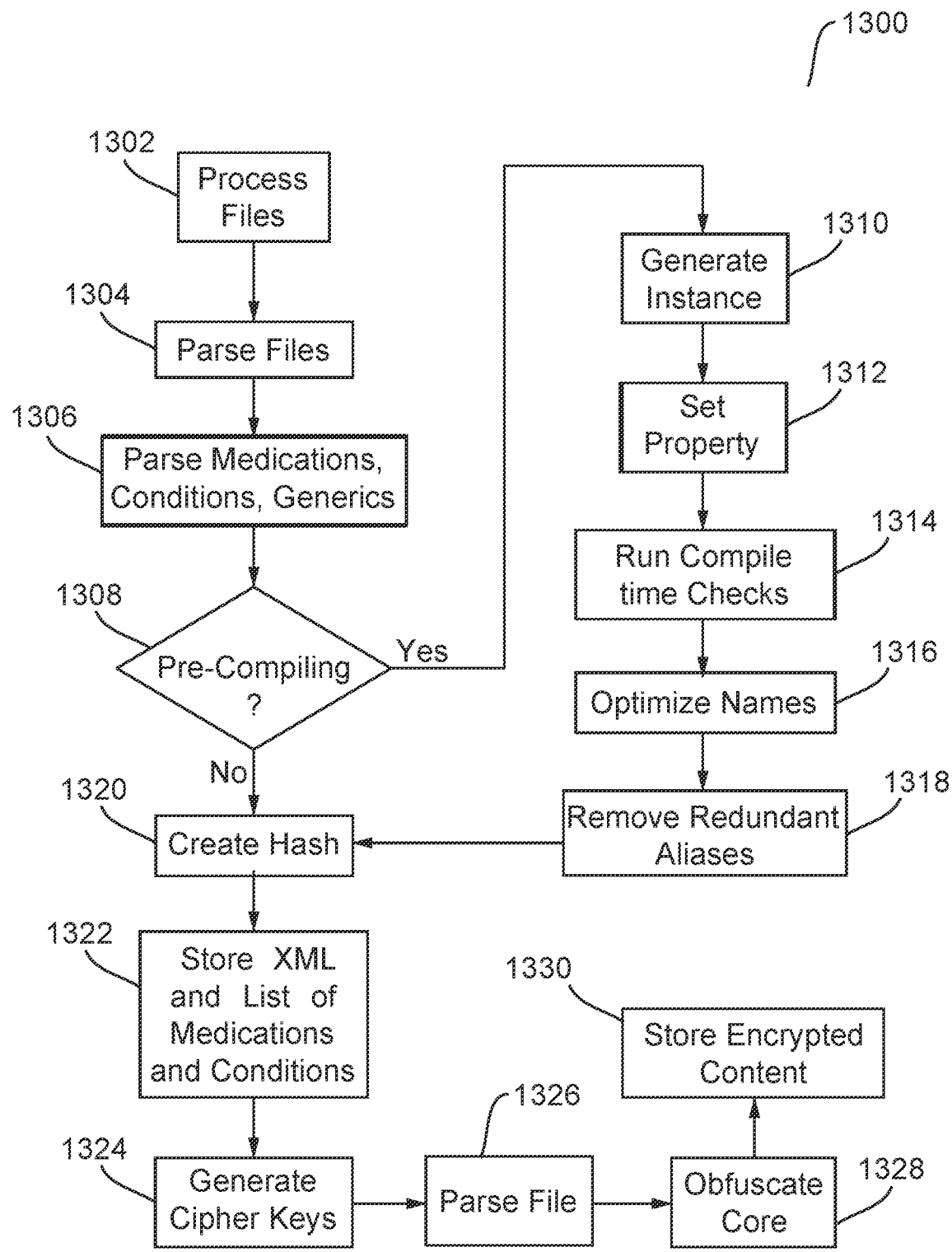
FIG. 13 illustrates a flowchart for generating the core according to the disclosed embodiments.

FIG. 13 depicts a flowchart 1300 for generating core 254 according to the disclosed embodiments. The disclosed process may be run by command or when a request is received from front end accessor 252. It may use code in a core base file as the root of the core and makes use of optional, but recommended, precompilation to store the data structures in a data component. If precompilation is not used, then the data component contains the concatenated XML interpolated from the plan files. The plan files may be structured in a specific manner according to the disclosed embodiments. This data may be encrypted.

Step 1302 executes by processing files that should be included in core 254. Step 1304 executes by parsing the files. The files are read and parsed into XML. This step takes data from the files to be included in the XML files or data structures. In other words, desperate files of data may be parsed to provide a set format for further processing. Step 1306 executes by parsing the medications, conditions, and generics as well as the aliases of each of these into their own lists, adding generics to the list of medications as well. The application of aliases is disclosed in greater detail below but its implementation also may be applied here.

Step 1308 executes by determining whether the core generation process is precompiling. If yes, then step 1310 executes by generating an instance for the proposed customer. For example, the instance may be someone of the age of 65 years. Step 1312 executes by setting the all plans property of the customer. Step 1314 executes by running compiletime checks. This step will allow the core to determine which plans have redundant components and keep track so the disclosed embodiments can use this information in the main analysis process disclosed below. Step 1316 executes by optimizing all restriction medication and condition names. Step 1318 executes by removing all redundant aliases in the list of aliases. Flowchart 1300 then proceeds to step 1320.

If step 1308 is no, then step 1320 executes by creating the content hash. Step 1322 executes by storing the XML and lists of medications and conditions as well as serializing it. This action binds together the database into the core file. Step 1324 executes by generating cipher keys from the serialized content hash and a secret key hardcoded into the program. Step 1326 executes by parsing the core base file to parse out a few internal signals, such as START_LITERAL and END_LITERAL.

Step 1328 executes by obfuscating the core file. This step may be implemented by a script. The script removes comments, strips multiple spaces, translates variable names to random strings from 4-21 characters based on the variable's length, removes empty lines, joins random lines, and the like. Step 1330 executes by storing the encrypted, serial content hash in the core data file. In a sense, the generated data is "frozen" until it is needed.

Figure 14:
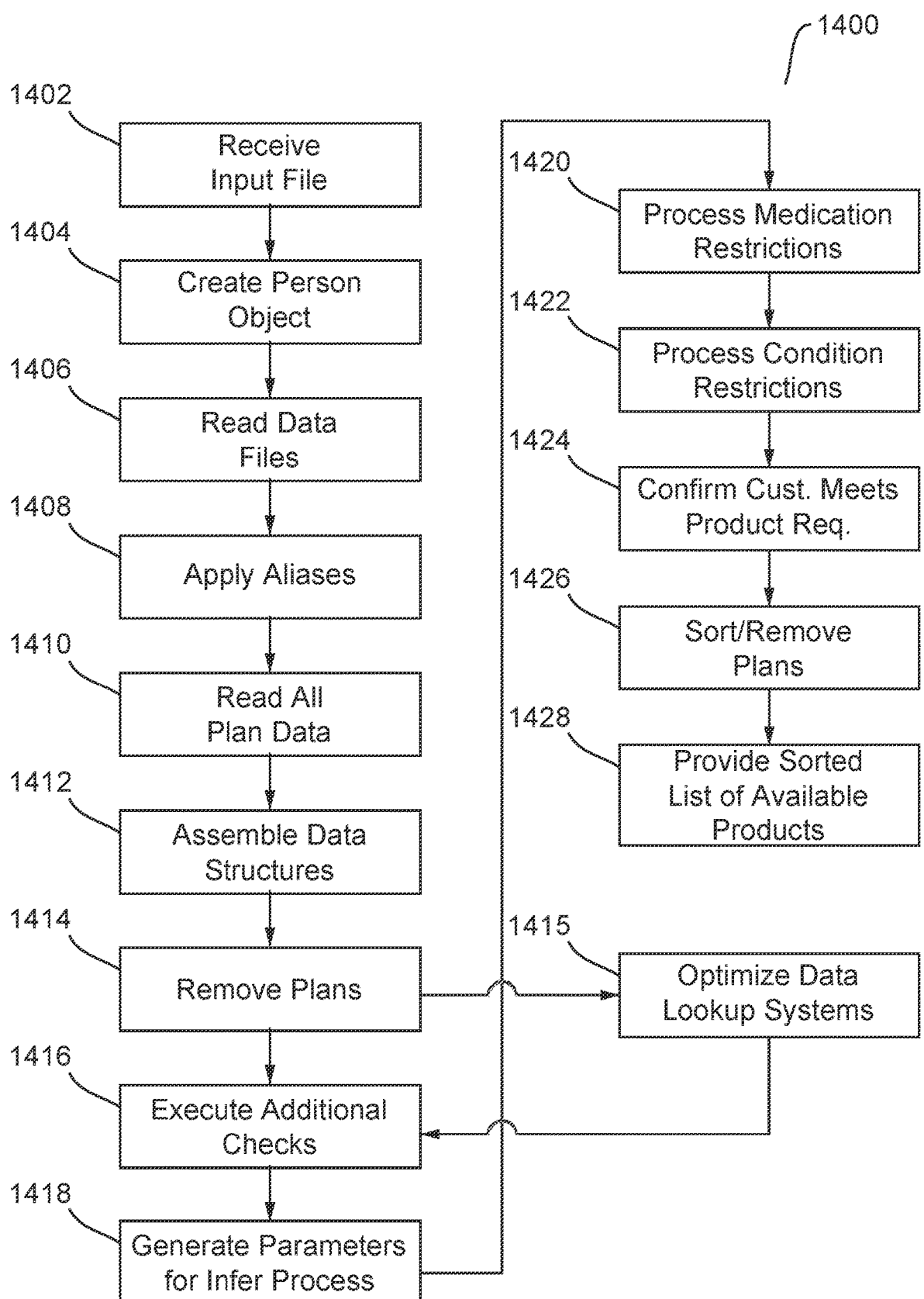
FIG. 14 illustrates a flowchart for performing the analysis of the compiled data using the core to select plans according to the disclosed embodiments.

Returning to flowchart 800, step 812 executes by analyzing the compiled data from front end accessor 252 using core 254 generated in step 810. Step 812 is disclosed in greater detail by flowchart 1400. FIG. 14 depicts a flowchart 1400 for performing the analysis of the compiled data using core 254 to select plans according to the disclosed embodiments. Step 1402 executes by receiving the input file, or compiled data structure 269. The input file also may be supplied via command line switches. The input file may be configured according to the following example (provided in the data modeling language, ZEDRAM):

```
(open person (set-attr (set height 59) (set weight 159) (set dob
    2-18-1993)))
    (open medications)
        (define-each (medication name/use/first_fill/last_fill)
            (
                Ventolin HFA/Asthama/8 years ago/1 year ago,
            )
        )
    (close medications)
    (open medical-conditions)
        (define-each (medical-condition
            name/last_treatment/was_diagnosed)
            (
                Asthma/3 months ago/12 years ago,
                Vocal Chord Dysfunction/3 years ago/6 years ago,
            )
        )
    (close medical-conditions)
(close person)
```

If an input file is not given, then the following information may be required according to the disclosed embodiments: height, weight, date of birth, medications, and conditions with medications including name, use, first fill, and last fill, and conditions including name, last treatment, diagnose date. There may be as many entries for medications and conditions as needed.

Step 1404 executes by creating a person object from parsed user data. The person object is generated using specific data from front end accessor 252. Step 1406 executes by reading all data files. In this step, the encrypted core data file may be decrypted. The disclosed embodiments may retrieve the data model from memory. Using the frozen example, the data structure of the core file is "unfrozen" to be used according to the disclosed embodiments.

Step 1408 executes by applying aliases. The disclosed embodiments may make use of an alias system, which is a tree-like structure designed to show the relationship between objects. The alias system of the disclosed embodiments is an inheritance-based system where the properties of the parent apply to the children or two properties should apply to each other. If a condition is a more generalized version of another condition, such as heart disorder and arrhythmia, the more specific version should be aliased to the more generalized version, thereby allowing the more specific version to inherit the restrictions of the more generalized version. That way, if a carrier restricts all heart disorders, then arrhythmia reflects that restriction.

The alias system of the disclosed embodiments reflects the expansion of conditions and the intelligent processing of conditions and medications in view of this expansion. The disclosed embodiments may include thousands of aliases. The alias system does not impact the user or customer. There may be different types of aliases. One-way aliases may be normal aliases that can be visualized as several leaves and other branches (new_names) growing off of a branch (original_name). For example, gestational diabetes should inherit the properties of diabetes. If a carrier restricts diabetes, then they also restrict gestational diabetes. The inverse is not necessarily the case.

Another type of alias is a circular alias. These are less intuitive aliases that can be understood to be synonyms. Any time two aliases mean the same thing, they are circular aliases. For example, nitroglycerine and nitroglycerin should be linked to each other. Thus, if one carrier restricts nitroglycerin and another restricts nitroglycerine, the restrictions should be applied without regard to how the customer's medication name is provided.

Aliases may be read from a global file. The global file outlines alias parents and children. The results are stored in hash lookups so that anyone can file relationships.

Step 1410 executes by reading all plan data. Plans may be stored in their own files. The file may be structured as shown below in the ZEDRAM data modeling language:

```
(open plans (set-attr (set brand am) (set product senior-choice)))
    ...general product family requirements:
    (define-each (additional-requirements requirement/type) (...))
    ...required:
    (open plan (set-attr (set name EXCLUDE) (set rank 5))) (close plan)
    ...foreach plan:
    (open plan (set-attr (set name NAME) (set rank RANK)))
        (define-each (height-weight inches/weight-min/weight-max) (...))
    (close plan)
    (open medications)
        (define-each (medication
            name/use/first_fill/last_fill/fill_within/plan) (...))
    (close medications)
    (open medical-conditions)
        (define-each (medical-condition
            name/criteria/last_treatment/was_diagnosed/additional_checks/plan)
            (...))
    (close medical-conditions)
(close plans)
```

Step 1412 executes by assembling the data structures.

Step 1414 executes by removing plans and product families that the customer, according to the person object and other data, does not qualify for. Steps 1415-1426 execute this step in detail. These steps may be executed for each plan. The disclosed embodiments are interested in removing plans as quickly as possible.

Step 1415 executes by preparing and optimizing data lookup systems, or optimizing the user model/person object by removing characters and other housekeeping processes, such as converting dates. Odd characters may be entered into data and is removed in this step. The disclosed embodiments may identify non-ASCII characters in the data structures.

Step 1416 executes by executing additional checks in the event there is a self-modifying check, such as something that prevents height-weight from being examined. The process of executing additional checks is disclosed in greater detail below.

Step 1418 executes by generating the parameters for the quasi-artificial intelligence process, which infer conditions based around medications, if requested by the plan or by the supplied user data. Step 1418 also may execute to infer these conditions. The disclosed embodiments may use the alias system disclosed above and the medication and condition lists to infer which conditions that the medications imply. For example, if the disclosed embodiments determine that the medication SPIRIVA indicates a respiratory disorder, then it will tell the disclosed embodiments to infer that the customer has every respiratory disorder, to be conservative as it is impossible to know which specific respiratory disorder applies without directly being given that information.

Figure 15:
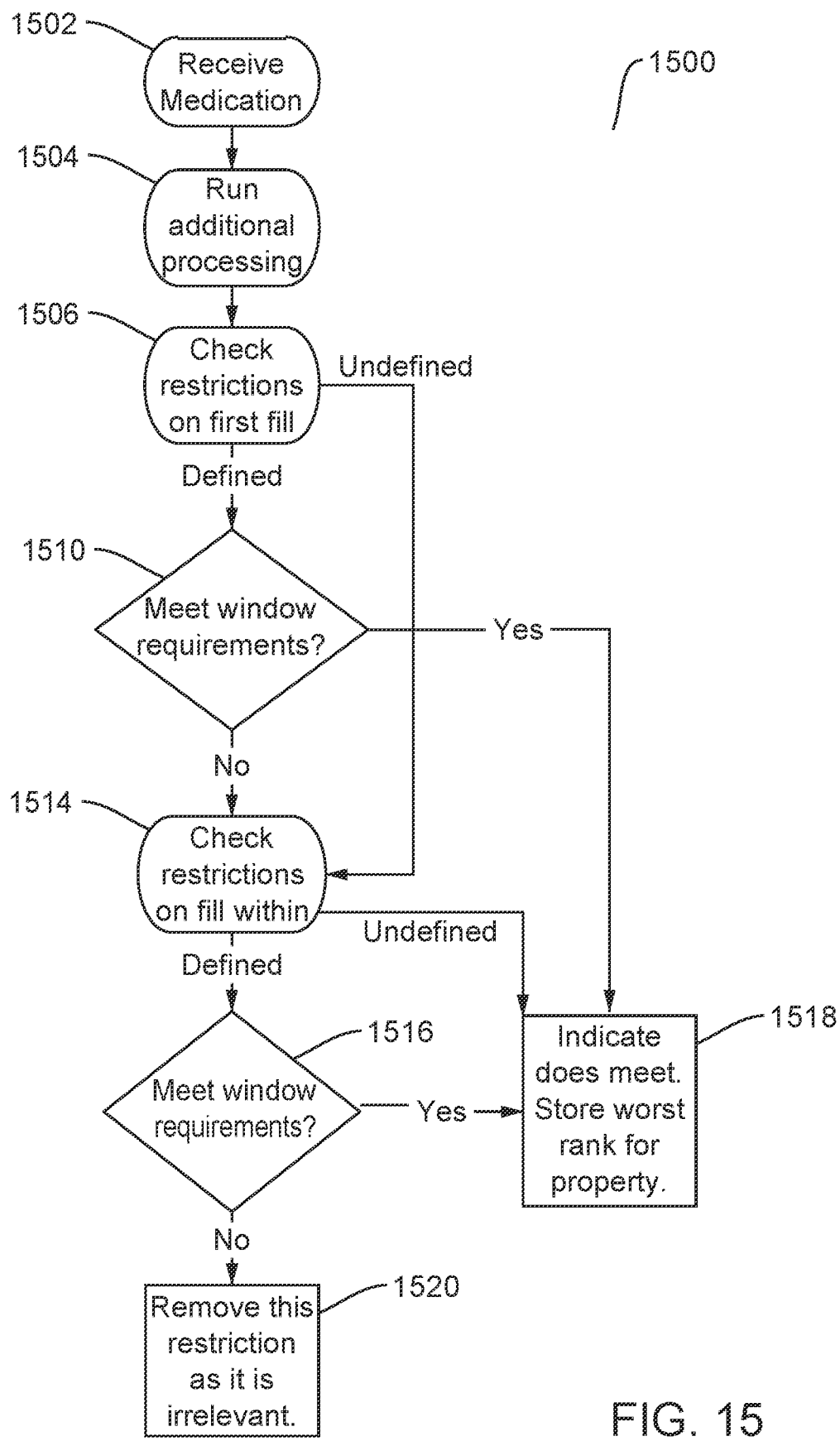
FIG. 15 illustrates a flowchart for processing medication restrictions according to the disclosed embodiments.

Step 1420 executes by processing medication restrictions to remove any superfluous restrictions. Step 1420 is disclosed in greater detail by flowchart 1500. FIG. 15 depicts a flowchart 1500 for processing individual medication restrictions according to the disclosed embodiments. Flowchart 1500 may be executed for each medication that the customer takes. Thus, step 1502 executes by receiving the medication name Step 1504 executes by running any additional processing on the medication. For example, acronyms or shortened names may be converted into the actual medical names for the medication.

Step 1506 executes by checking for restrictions on the first fill for the medication. The plan may have a restriction on when the first fill of the prescription may be accepted. In other words, the plan does not want to cover a condition that has been treated for several years according to the first fill of the applicable medication. Step 1510 executes by determining whether the customer takes the medication within the window provided by the first fill restriction.

If step 1510 is yes or step 1506 determines there are no restrictions for the first fill parameter, then step 1514 executes by determining a fill within restriction for the plan. If the medication is outside the first fill window or the plan does not impose a restriction on the first fill parameter, then the disclosed embodiments check to see if the customer took the medication within a fill within window. The fill within and last fill windows are synonyms. Step 1516 executes by determining whether the customer, according to the person object, takes the medication within the window provided by the fill within restriction. If no, then step 1520 executes by removing the restriction as it is unrelated to the person object. If step 1514 is not defined or 1516 is yes, then the restriction is valid and the restriction and its rank are stored in step 1518.

Figure 16:
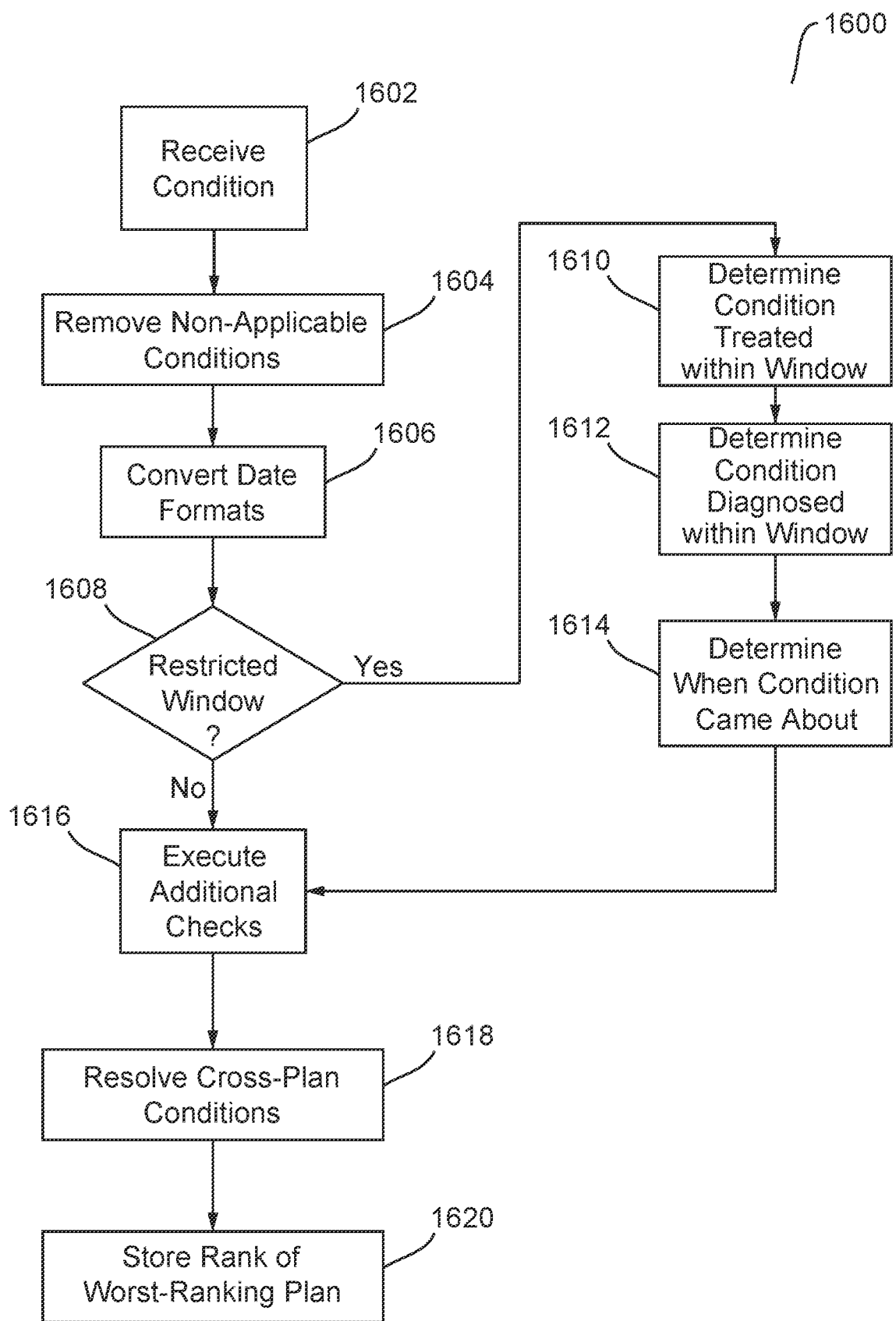
FIG. 16 illustrates a flowchart for processing condition restrictions according to the disclosed embodiments.

Returning back to flowchart 1400, step 1422 is executed by processing the condition restrictions for each condition within the person object for the customer. Step 1422 is disclosed in greater detail by flowchart 1600. FIG. 16 depicts a flowchart 1600 for processing condition restrictions according to the disclosed embodiments. Step 1602 executes by receiving the condition from the person object. Step 1604 executes by removing non-applicable conditions. This process may mimic the process outlined in flowchart 1500 replacing first fill with diagnosis date and fill within with last treatment. Step 1606 executes by converting date formats into the format consistent with the disclosed embodiments.

Step 1608 executes by determining whether a restricted window for the condition was defined by the plan. If yes, then step 1610 executes by determining if the condition was treated within a restricted window. Step 1612 executes by determining if the condition was diagnosed within the restricted window. Step 1614 executes by determining if the condition came about during the restricted age of onset window if a restricted window was defined at all.

If step 1608 is no, and after execution of steps 1610-14, then step 1616 executes by executing any additional checks defined by the plan or product family Additional checks may be call functions inside the code executing the disclosed processes. The additional checks may be plan or product specific. They allow for dynamic rules to expand the capabilities of the disclosed processes. If certain conditions are met, then additional actions may be taken. The intention of additional checks is to prevent redundancy. Thus, there will be times where there are additional checks that should actually be parsed into its own rule-based system instead of in the additional checks system. The additional checks may further remove plans from consideration.

Step 1618 executes by resolving cross-plan conditions. One condition may have multiple applicable plan options, so the worst ranking applicable option is chosen. Step 1620 stores the rank of the worst-ranking plan for the product family.

Returning to flowchart 1400, step 1424 executes by confirming the customer meets product requirements. Such requirements may include height and weight requirements. As noted above, each product may include at least two plans. If the customer does not meet the requirements for the product, then these plans may be removed from consideration.

Figure 17:
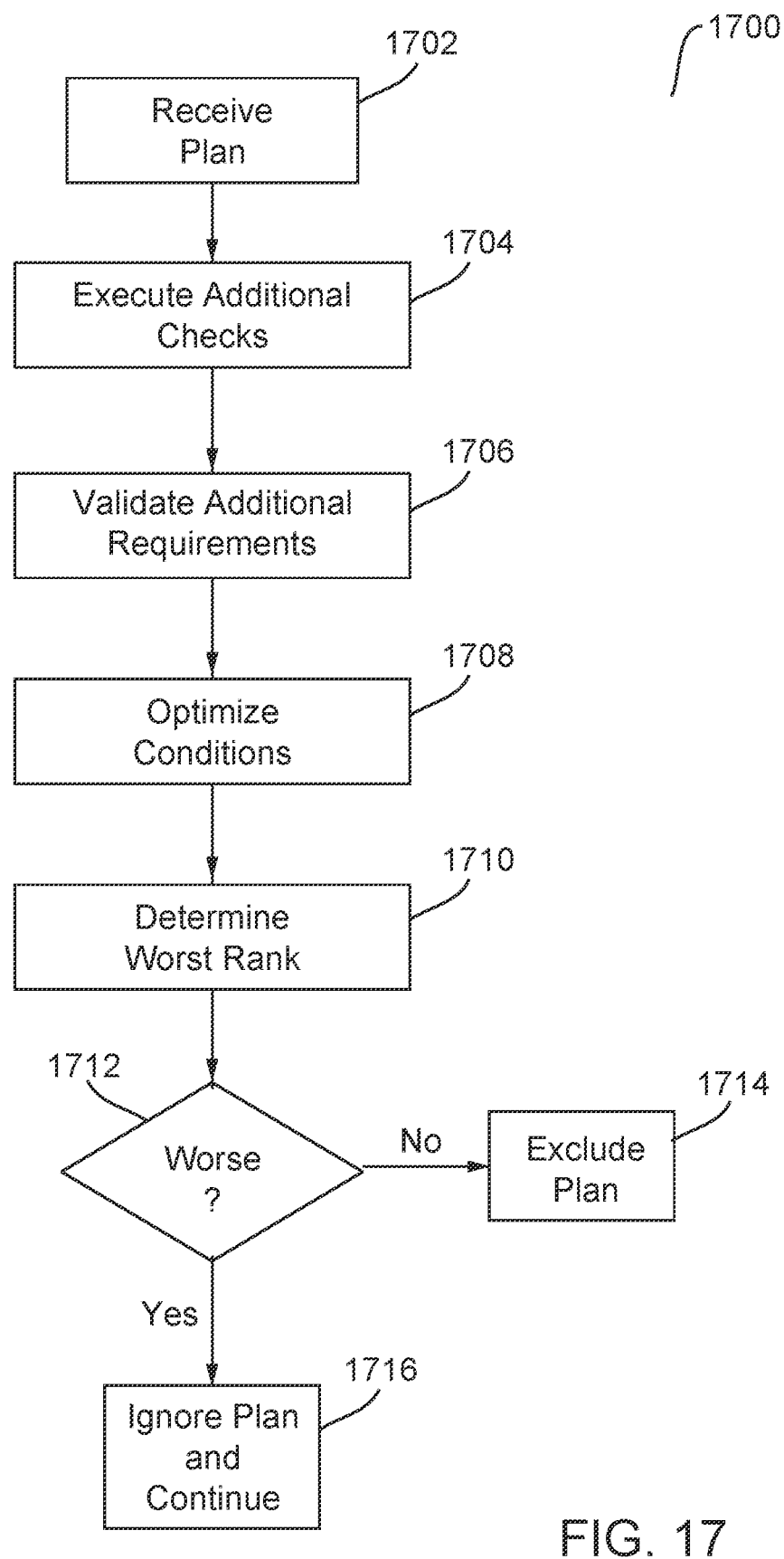
FIG. 17 illustrates a flowchart for sorting and removing plans according to the disclosed embodiments.

Step 1426 executes by sorting and removing plans. Step 1426 is disclosed in greater detail by flowchart 1700. FIG. 17 depicts a flowchart 1700 for sorting and removing plans according to the disclosed embodiments. Step 1704 executes by executing the additional checks process disclosed above for each plan and product family. The disclosed embodiments run additional checks to validate that the plan's additional requirements are satisfied in step 1706. If not, then exclude the plan.

Step 1708 executes by optimizing properties of the customer to remove duplicates, to merge overlapping conditions of the same name, and the like. Step 1710 executes by determining the worst rank that the customer qualifies for based around the medications and conditions, as determined above. Step 1712 executes by determining whether that worst rank is worse than the rank of the current plan. If no, then step 1714 executes by excluding the plan. If yes, then step 1716 moves on to the next plan staged for analysis until no more plans are staged for analysis.

Returning back to flowchart 1400, step 1428 executes providing the sorted list of all available products to the user, who then may present them to the customer. The plans are pared down to remove inapplicable plans or plans that will not meet the carrier's requirements or the customer's needs and only the best ranking plan for each product family is displayed. Thus, agents do not waste time marketing plans that the customer does not qualify for.

Further examples of disclosed embodiments enable the generation of insurance recommendations that supports user medical conditions without requiring a user to provide exhaustive medical information. By receiving user input of various medication information and using this as input to a selection model, the autocond migration module enables the inference of potential patient medical conditions without requiring the user to input this information directly. The inferred conditions are then used as input to the policy selection process and deleted. In this way, the disclosed embodiments can identify insurance policies that support a user's potential medical condition support needs without requiring the input of or the storage of user medical information.

As discussed with reference to FIGS. 12-14 above, the various embodiments may use a selection model, including data structures such as data structures 274 and 276. The selections model may include an artificial intelligence model in conjunction with one or more data structures. That is, the selections model may be a quasi-artificial intelligence model as it includes both artificial intelligence models and other data structures. The selections model may be stored in the data storage 43 of the platform 40 and may receive as input, data related to buyer medications that has been transmitted to the platform 40 from any of the devices 25, 35 via network 15.

In some embodiments the artificial intelligence models of the overall selection model may be collectively referred as the conditions model and may include random forests or expert systems. For example, the conditions data structure 276 and medications data structure 274 may be part of a random forest having nodes that contain information about various medical conditions and the medications prescribed to treat the conditions. In another example, the conditions data structure 276 and the medications data structure 274 may be separate structures forming expert systems. In either example, the conditions model may have a tree structure with vertical and lateral connections between nodes.

The conditions model may be trained or built using a data set of known medical conditions, symptoms, and statuses, as well as known medications and their generic counterparts. Some or all of the dataset may be obtained from the sellers (i.e. insurers), the public disclosures of pharmaceutical companies, and other external sources. The data set used to build the conditions model includes the formal names of medications, known generic names of the medication, the on-label conditions for which the conditions are prescribed, the off-label conditions for which the medication is prescribed, the dosage information for treating each condition and other prescribing information such as duration of treatment and refill rates. Additional medication related information such as side effects, manufacturer, and the like may also be collected and used to build the conditions model.

Each node of the conditions model may have a key entry that is a medical condition. The conditions model has a tree structure in which the primary identifier for each node is a medical condition to which a pointer of the tree structure is directed. The nodes further contain data including medications used to treat the condition for on-label user; medications used to treat the condition for off-label use; prescribing and dosing information for each medication listed; classes or types of medications that may be used interchangeably to treat the condition; and groups of medications or medication classes that taken in combination may treat the condition. Further, each node of the conditions model may contain severity ranges indicating a frequency of refill that correlates to a severity or persistence of the medical condition. For example, a severity range of 1-5 refills per year for a particular mediation may be associated with mild severity and, or acute presentation of the condition. Refill frequencies falling above this range may thus indicate chronic presentation of the condition or heavy severity.

The resulting conditions model may be hierarchical and organized by condition such that broad categories of conditions are located in top-nodes of the tree(s). For example, an upper node of the conditions model may include "respiratory conditions" and dependent nodes may become increasingly granular with respect to the conditions they contain, e.g., respiratory inflammation, then asthma or bronchitis, then chronic bronchitis of COPD. Each node may include not only the name of the condition, but also the names of medications, their associated generics, and dosing information for treating the condition with which the node is associated. Reference pointers within each node may point to not only lower level nodes, but also to other nodes with which a medication is associated. Thus, a node of the conditions model may have a set of reference pointers associated with more specific conditions (i.e. lower level conditions within the tree) and also a set of reference pointers pointing from the listed medications to other nodes. The finished conditions model may be searched to identify user medical conditions based on the medications prescribed to the user.

In order to obtain medication information in sufficient detail to generate a query for the conditions model, the buyer device 25 may provide a graphical user interface with text input fields for receiving medication information. On-screen prompts may be displayed requesting that the user provide input of the names of current medications. Along with the names of current medications, the prescribed dosage for each medication, the number of remaining refills for the medication and the date of the last fill of the medication may be provided. Optionally, the condition for which the medication was prescribed may also be input into a corresponding text field.

Entered medication information is transmitted by the device 25 to the platform 40 for identification and validation of buyer medical conditions. The user input associated with each individual medication is used to structure a search query or input vector for the conditions model. The platform 40 may receive the medication information via an API connecting to the device 25 graphical user interface. Information may be received for each medication in turn or collectively after entry of all medications. In either instance, the processor of the platform 40 may sort, correct, error-check, and separate or combine medication information in preparation for building search queries or input vectors for the conditions model.

Prior to identifying buyer medical conditions, the platform may use the selection model, i.e., the medications data structure 274, to error-check and correct medication names as input by the buyer. Medications often have names that are generated based not the chemical compounds they contain and are thus unfamiliar in sound and spelling to the average user. It is common for medication users to spell the names of the medications they take phonetically, using nicknames, shortened spellings or other incorrect terms. To address this issue and improve the accuracy of conditions model output, the selection model may use the medication information to search the medications data structure 274 for known variations of the medication names. The search may begin by searching or crawling the medications data structure 274 for the exact spelling of the medication name as provided by the buyer. If a match is detected between a data structure key entry, i.e. the proper medication name, and the medication name, then the search quits and processor moves on to the next medication name provided by the buyer. However, the medications data structure 274 search is not limited to key entries. Each key entry is stored in association with common misspellings of the name, along with known generic names for the medication. These misspellings and generic names may be grouped to enable easy determination of whether the provided medication name is a misspelling of the key entry or a generic variation of the key entry. Once the correct misspelling or generic variation is identified, the corresponding key entry, i.e. the formal medication name, is added to a corrections list alongside the original user input.

If no entry matching the buyer provided medication name exists within the medications data structure 274, then the platform may, in any order, perform at least one of two operations. One operation to be executed by the processor of the platform 40 is to perform a character-wise comparison of the buyer provided input to the key entries and generic names. This type of search may be resource-intensive and thus various searching algorithms may be employed to accommodate the size and scope of the medications data structure 274. The result of the character-wise comparison is an entry that most closely matches the buyer provided input. For example, the search may return the entry having the highest percentage of characters in common with the buyer provided input. This "best fit" entry, whether it is a key entry or a generic name, may be added to the corrections list along with the buyer provided input.

Another option for addressing missing medication names is to perform an internet search for the buyer provided input. The processor of the platform 40 may execute an API for an internet-based search engine to perform a general search for instances of the buyer-provided input. The results of the search query are then parsed by the processor of the platform 40 to determine if the buyer provided input is a medication name appearing on a website of a known drug manufacturer. Dosage and usage information may also be scraped from the manufacturer website. The formal medication name, dosage, and prescribing information may be added to the medications data structure using the formal medication name as a key entry. In embodiments in which the conditions model is not distinct from the medications data structure 274, the new medication may be added to the conditions model using the conditions for which the medication is prescribed as key node identifiers. For example, if a new medication "X" is described as used for treating athlete's foot, the medication may be added under medications information for the node of the condition "athlete's foot." The new medication is then added to the corrections list along with the buyer provided input.

The corrections list is transmitted to the buyer device 25 for display via the graphical user interface. The user may be prompted to review the items in the corrections list to confirm that the corrected medication names Selection icons may be displayed next to correction list entries to enable a buyer to individually confirm the medication name corrections that are accurate. Once the buyer has confirmed the accuracy of corrections, the confirmation is transmitted to the platform 40 in a confirmation message. If the buyer rejects some of the corrections, the buyer may be prompted to contact customer service. Alternatively, the methods may continue without the disputed medication.

Once the medication information input by the buyer has been corrected or waived, the platform 40 uses the updated medication information to build a search queries or input vectors for each of the mediations provided. For each medication provided by the buyer, the processor of the platform 40 may submit the medication name and associated information to the conditions model. The processor may execute the conditions model, which may search for the first instance of a mediation appearing in a node in association with a condition, the condition and all conditions appearing above the node in the tree will be added to a conditions list. For example, a medication used to treat eczema may appear in the conditions model node for eczema. Nodes vertically linked to the eczema node may include "allergic reactions," "skin rashes," "skin conditions," "immune disorders," etc. Each of these conditions is added to the conditions list for review by the buyer. Link pointers may point from the medication in the condition node to the condition nodes of all other conditions for which the medication is prescribed. Each of the link pointers is followed to the corresponding condition node and the condition is added to the conditions list along with the conditions for each node vertically linked to that condition node. Thus, the processor may look for medications within the leaves of the tree and may add not only each leaf, but the branch supporting the leaf to the conditions list.

In some embodiments, identified conditions may also be presented to the user in a feedback-loop process in which a medication or condition may imply a specific other condition and that condition should be displayed to the user in the conditions list. For example, if a user supplied a medication name prescribed for the treatment of a Diabetic Coma, the conditions model also identifies the condition Diabetes and adds Diabetes into the conditions list. Similarly, if the user adds the condition Paraplegia while providing feedback input to the conditions list, an additional condition about their use of a wheelchair may be identified by the conditions modle and added to the updated conditions list.

In some instances, the dosage information for the medications may be relevant to the identification of conditions. The search query or input vector may be used by the processor to search for condition model nodes that contain not only the medication name, but also a prescribing dosage range that encompasses the dosage information provided by the buyer. For example, a medication "X" submitted by the buyer with dosage of 100 mg may produce a search of the conditions model that returns only conditions for which X is prescribed at a dosage range that includes 100 mg.

In addition to executing the conditions model on each medication individually, the processor may also build compound search queries or input vectors for input to the conditions model. Compound queries are built using medication information for multiple medications provided by the buyer. For example, medications of the same class or type may have their dosages combined to form a search query or input vector based on the total dosage for the medication class or type. The medications "aspirin" and "ibuprofen" if listed by a buyer would result in not only individual searches for the two medications, but also a search for the class or type of "non-steroid anti-inflammatory drugs (NSAIDs)." Each of the individual searches is presented with the dosage information and prescription fill information for the individual medications, however the "NSAIDS" class or type may be submitted for search along with the collective or cumulative dosage information. Output from applying the NSAIDs information to the conditions model may be a set of conditions for which NSAIDs are prescribed with a dosage range that includes the cumulative dosage. This condition set may be added to the conditions list to the extent that the entries are not duplicative. However, this conditions set may also be applied as a filter to the conditions list to narrow the or trim the list of conditions. Continuing the above example, a conditions list that includes metrics that qualify under "aspirin" and "ibuprofen" individually may lack sufficient dosage to qualify under the class of NSAIDs at the cumulative dosage. The processor may remove from the conditions list any conditions that to not include the cumulative NSAIDs dosage within their prescription ranges.

Thus, if the buyer is taking a cumulative 500 mg of NSAIDs, the condition "minor muscle ache" with a medication of "ibuprofen" and a dosage of "100 mg" may be removed from the conditions list. Alternatively, conditions that would be filtered out by the cumulative class or type dosage, may be flagged instead for user review.

Further, the various embodiments provide for the identification of buyer medical conditions based on the combination of medications a buyer provides. This functionality is enabled through the storing of not only individual medication names and classes/types in condition nodes of the conditions model, but also medication groups or combinations. The search query or input vector for the conditions model can include a list of all medication names. When one of the medication names is identified within a node of the conditions model, the processor of the platform 40 checks to determine if other medications listed within the input vector are also included in the identified conditions node. Some condition nodes may include predominantly medication combinations over individual a medication names. This is because some more complicated conditions, such as "long COVID" may require a combination of medications in order to adequately address symptoms of the condition. In some embodiments, there may be conditions that are only treatable through a combination of medications, and thus the search query/input vector for the combination of buyer provided medications may be the only search query that returns the condition. Conditions identified through combination medication queries are also added to the conditions list for buyer approval.

Although the search queries and input vectors discussed above are described as individual inputs to the conditions models, this is not the only method of providing input to the conditions model. For the sake of providing a clear disclosure, the input vectors/search queries are described individually. However, the input may be provided in a single input vector, in which all the buyer-provided medication information (i.e., medication names, dosage information, refill information, etc.) is provided in a predetermined format. For example, the input vector might be:

$$\{a_1,[b \ldots b_n],[c \ldots c_n];a_2,[b \ldots b_m],[c \ldots c_m];a_x\}$$

Where a is a condition, b is the medications prescribed to treat that condition, and c is the dosage information for corresponding medications. Additional information such as the refill information, medication classes, and the like, may be included in the input vector. The above vector is shown for exemplary purposes and is not intended to be exhaustive.

Once the output of the conditions model is received for all medications, medication classes, and medication groups, the conditions list is transmitted to the buyer device 25 for display via the graphical user interface. The conditions list displayed to the buyer is interactive, having selectable buttons for accepting or rejecting conditions displayed within the conditions list. The buyer user may review the conditions list and use the input device of the client device 26 to accept or reject the displayed conditions. If the buyer does not have a condition displayed in the conditions list, they select a rejection button or deselection the condition from the conditions list. The buyer may then submit the updated corrections list using a button on the graphical user interface. The updated conditions list is transmitted to the platform 40. The processor of the platform 40 may remove the conditions that were rejected or deselected by the buyer from the conditions list. The result of removing rejected conditions from the conditions list is a health profile. This health profile is input for plan selection. The process may continue on to the methods described in FIGS. 14-17 to select plans that support the conditions indicated in the updated conditions list represented in the health profile. The platform 40 may use the health profile as input to the plans and policies evaluation processes in order to identify insurance plans that do not exclude the conditions listed in the health profile. Alternatively, the health profile may be used to minimize the number of conditions that are not covered by identified insurance plans, thus displaying to the buyer only those insurance plans that cover the highest number of conditions listed in the prescribing guide.

The above-described embodiments provide solutions to the problem of accurately identifying insurance plans or policies that will support a consumer's various medical conditions, without requiring the user to fully disclose their medical condition status or be fully accurate with their provided information. Because consumers are not always forthcoming with their medical conditions, or are not sure of the name or spelling of their conditions, it can be difficult for insurance carriers to identify and suggest plans that will support and cover the consumer's medical conditions. The disclosed embodiments provide for the building and implementation of a selection model that includes an artificial intelligence conditions model and other data structures to build a list of consumer medical conditions using the consumer's provided list of medications rather than their specific medical conditions. In this way, the disclosed embodiments leverage AI techniques to identify relationships between medications and medical conditions in order to infer a consumer's medical conditions without actual knowledge of those conditions. The selection models component models enable the platform to overcome failures by consumers to provide accurate or complete medical conditions information, and still produce an accurate list of the user's conditions to an insurance plan selection model.

It is to be understood that the above description is intended to be illustrative, and not restrictive. Many other implementations are apparent upon reading and understanding the above description. The scope of the disclosure should, therefore, be determined with reference to the appended claims, along with the full scope of equivalents to which such claims are entitled.

In the above description, numerous details are set forth. It is apparent, however, that the disclosure may be practiced without these specific details. In some instances, structures and devices are shown in block diagram form, rather than in detail, in order to avoid obscuring the disclosure.

Some portions of the detailed descriptions above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the following discussion, it is appreciated that throughout the description, discussions utilizing terms such as "receiving", "determining", "identifying", "updating", "copying", "publishing", "selecting", "utilizing" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The disclosure also relates to an apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems appears as set forth in the description below. In addition, the disclosure is not described with reference to any particular programming language. It is appreciated that a variety of programming languages may be used to implement the teachings of the disclosure as described herein.

The disclosure may be provided as a computer program product, or software, that may include a machine-readable medium having stored thereon instructions, which may be used to program a computer system (or other electronic devices) to perform a process according to the disclosure. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), a machine (e.g., computer) readable transmission medium (electrical, optical, acoustical or other form of propagated signals (e.g., carrier waves, infrared signals, digital signals, etc.)), etc.

It is to be understood that the above description is intended to be illustrative, and not restrictive. Many other implementation examples are apparent upon reading and understanding the above description. Although the disclosure describes specific examples, it is recognized that the systems and methods of the disclosure are not limited to the examples described herein, but may be practiced with modifications within the scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

The invention claimed is:

1. A method for identifying a plan from a plurality of plans, the method comprising:
    generating, by a processor of a computing platform, a digital personal representation of user data, wherein the user data includes parameters that apply to a person object for the personal representation;
    receiving, from a buyer computing device, medication information for a customer related to the person object, the medication information including medication name, dosage information, and refill information, wherein the medication information is input via an input device of the buyer computing device;
    activating a front end accessor at the buyer computing device by
        generating credentials for the customer at the front end accessor, wherein the credentials include a license key generated based on information about the customer at the front end accessor and a random string corresponding to the front end accessor, and
        authenticating the front end accessor using the license key and the random string;
    providing the license key to a communication server, wherein the communication server is communicatively coupled to the front end accessor and a core;
    providing an artificial intelligence model from the core to the front end accessor, wherein the artificial intelligence model includes a conditions data structure and a medications data structure;
    generating, by the processor, at least one input vector, based on the received medication information;
    executing, by the processor, the artificial intelligence model on the at least one input vector to generate a list of medical conditions that the customer may be experiencing;
    comparing, by the processor, the list of medical conditions to plan exclusion criteria and the provided parameters to identify excluded plans;
    removing the excluded plans from a list of available plans; and
    transmitting, to the buyer computing device, a list of plans that fit the provided parameters and were not excluded for display to the buyer.

2. The method of claim 1, further comprising:
    searching a medications data structure for each of the medication names in the received medication information to determine whether the medication name appears in the medications data structure;
    in response to determining that the medication name does appear in the medications data structure, determining if the medication name is not one of a formal medication name or a generic medication name;
    in response to determining that the medication name is not one of a formal medication name or a generic medication name, identifying the formal medication name that most closely matches the medication name;
    adding the medication name and the matched formal medication name to a corrections list; and
    transmitting the corrections list to the buyer computing device for display to the user;
    receiving, from the buyer computing device, user input accepting or rejecting the medications in the corrections list; and
    for each accepted correction in the corrections list, replacing the medication name in the received medical information with the accepted formal medication name.

3. The method of claim 2, wherein the medication information used to generate the input vector includes the corrected medication names in place of the originally received medication names that were corrected via the corrections list.

4. The method of claim 2, further comprising:
in response to determining that the medication name does not appear in the medications data structure, accessing an internet search application programming interface (API) to search medication manufacturer websites for the medication name; and
in response to determining that the medication name was found on a medication manufacturer website, adding the medication name and corresponding dosage and prescribing information from the website to the medications data structure.

5. The method of claim 2, wherein the medications data structure is part of the artificial intelligence model.

6. The method of claim 1, wherein the refill information includes a number of refills remaining and the last refill date.

7. The method of claim 1, further comprising
generating, by the processor, at least one combination input vector, including combinations of medications provided in the received medication information; and
executing, by the processor, the artificial intelligence model on the combined input vector to generate a list of medical conditions the customer may be experiencing.

8. The method of claim 1, further comprising
generating, by the processor, at least one class input vector, including a class of medications provided in the received medication information along with a combined dosage of all medications of that class listed in the received medication information;
executing, by the processor, the artificial intelligence model on the class input vector to generate a list of medical conditions the customer may be experiencing.

9. A method for identifying a plan from a plurality of plans, the method comprising:
generating, by a processor of a computing platform, a digital personal representation of user data, wherein the user data includes parameters that apply to a person object for the personal representation;
receiving, from a buyer computing device, medication information for a customer related to the person object, the medication information including medication name, dosage information, and refill information, wherein the medication information is input via an input device of the buyer computing device;
activating a front end accessor at the buyer computing device by
generating authentication credentials for the user at the front end accessor, and
authenticating the front end accessor using the authentication credentials;
providing the authentication credentials to a communication server, wherein the communication server is communicatively coupled to the front end accessor and a processing logic;
activating artificial intelligence parameters in the front end accessor from proprietary databases through the communication server, the proprietary databases including a conditions data structure and a medications data structure;
executing, by the processor, a process using the artificial intelligence parameters to generate a list of medical conditions that the customer may be experiencing;
comparing, by the processor, the list of medical conditions to plan exclusion criteria and the provided parameters to identify excluded plans;
removing the excluded plans from a list of available plans; and
transmitting, to the buyer computing device, a list of plans that fit the provided parameters and were not excluded for display to the buyer.

10. The method of claim 9, further comprising:
searching a medications data structure for each of the medication names in the received medication information to determine whether the medication name appears in the medications data structure;
in response to determining that the medication name does appear in the medications data structure, determining if the medication name is not one of a formal medication name or a generic medication name;
in response to determining that the medication name is not one of a formal medication name or a generic medication name, identifying the formal medication name that most closely matches the medication name;
adding the medication name and the matched formal medication name to a corrections list; and
transmitting the corrections list to the buyer computing device for display to the user;
receiving, from the buyer computing device, user input accepting or rejecting the medications in the corrections list; and
for each accepted correction in the corrections list, replacing the medication name in the received medical information with the accepted formal medication name.

11. The method of claim 10, further comprising:
in response to determining that the medication name does not appear in the medications data structure, accessing an internet search application programming interface (API) to search medication manufacturer websites for the medication name; and
in response to determining that the medication name was found on a medication manufacturer website, adding the medication name and corresponding dosage and prescribing information from the website to the medications data structure.

12. The method of claim 9, wherein the refill information includes a number of refills remaining and the last refill date.

* * * * *

UNITED STATES PATENT AND TRADEMARK OFFICE
CERTIFICATE OF CORRECTION

| | | |
|---|---|---|
| PATENT NO. | : 12,175,539 B2 | Page 1 of 1 |
| APPLICATION NO. | : 17/739663 | |
| DATED | : December 24, 2024 | |
| INVENTOR(S) | : Zach Bornheimer | |

It is certified that error appears in the above-identified patent and that said Letters Patent is hereby corrected as shown below:

On the Title Page

Item (63), should read as follows:
Related U.S. Application Data
(63) Continuation-in-Part of Application No. 16/701,960, filed on Dec. 3, 2019, now abandoned, which claims benefit of Provisional Application No. 62/774,641, filed on December 3, 2018.

Signed and Sealed this
Thirteenth Day of May, 2025

Coke Morgan Stewart
*Acting Director of the United States Patent and Trademark Office*